(12) United States Patent
Fiedler et al.

(10) Patent No.: US 12,257,277 B2
(45) Date of Patent: *Mar. 25, 2025

(54) ADENO-ASSOCIATED VIRUS FORMULATIONS

(71) Applicant: TAKEDA PHARMACEUTICAL COMPANY LIMITED, Osaka (JP)

(72) Inventors: Christian Fiedler, Vienna (AT); Eva Fritscher, Vienna (AT); Meinhard Hasslacher, Vienna (AT); Dominik Mittergradnegger, Vienna (AT); Tanvir Tabish, Kent (GB)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/096,853

(22) Filed: Jan. 13, 2023

(65) Prior Publication Data

US 2023/0241139 A1    Aug. 3, 2023

Related U.S. Application Data

(63) Continuation of application No. 16/347,107, filed as application No. PCT/US2017/059971 on Nov. 3, 2017, now Pat. No. 11,583,563.

(60) Provisional application No. 62/417,750, filed on Nov. 4, 2016.

(51) Int. Cl.
| | |
|---|---|
| A61K 35/76 | (2015.01) |
| A61K 9/00 | (2006.01) |
| A61K 9/19 | (2006.01) |
| A61K 31/195 | (2006.01) |
| A61K 47/18 | (2017.01) |
| A61K 47/26 | (2006.01) |
| A61P 7/00 | (2006.01) |
| A61P 7/04 | (2006.01) |

(52) U.S. Cl.
CPC ............ *A61K 35/76* (2013.01); *A61K 9/0019* (2013.01); *A61K 9/0053* (2013.01); *A61K 9/19* (2013.01); *A61K 31/195* (2013.01); *A61K 47/183* (2013.01); *A61K 47/26* (2013.01); *A61P 7/00* (2018.01); *A61P 7/04* (2018.01)

(58) Field of Classification Search
CPC .... A61K 35/76; A61K 9/0019; A61K 9/0053; A61K 9/19; A61K 31/195; A61K 47/183; A61K 47/26; A61K 47/02; A61K 47/18; A61K 47/22; A61K 9/00; A61K 9/08; A61P 7/00; A61P 7/04; C12N 15/86
See application file for complete search history.

(56) References Cited

U.S. PATENT DOCUMENTS

| | | |
|---|---|---|
| 6,764,845 B2 | 7/2004 | Sista |
| 9,051,542 B2 | 6/2015 | Wright |
| 2002/0041884 A1 | 4/2002 | Evans |
| 2003/0153065 A1 | 8/2003 | Kovesdi et al. |
| 2004/0166122 A1 | 8/2004 | Evans |
| 2011/0229455 A1 | 9/2011 | Matthiessen et al. |
| 2012/0141528 A1 | 6/2012 | Coffey |
| 2016/0199496 A1 | 7/2016 | Jezek et al. |
| 2017/0130208 A1 | 5/2017 | Potter et al. |

FOREIGN PATENT DOCUMENTS

| | | |
|---|---|---|
| JP | H1990503266 | 10/1990 |
| JP | H1997504429 | 5/1997 |
| JP | 2002506048 | 2/2002 |
| JP | 2003525909 | 9/2003 |
| JP | 2011517955 | 6/2011 |
| JP | 2012143233 | 8/2012 |
| JP | 2014501493 | 1/2014 |
| WO | 198906542 | 7/1989 |
| WO | 199510601 | 4/1995 |
| WO | 199945966 | 9/1999 |
| WO | 2001066137 | 9/2001 |
| WO | 2005118792 | 12/2005 |
| WO | 2013036961 | 3/2013 |
| WO | 2013130393 | 9/2013 |
| WO | 2015040234 | 3/2015 |
| WO | 2015121501 | 8/2015 |

(Continued)

OTHER PUBLICATIONS

Monahan PE. Gene therapy in an era of emerging treatment options for hemophilia B. J Thromb Haemost. Jun. 2015; 13 Suppl 1(0 1):S151-60. doi: 10.1111/jth.12957. PMID: 26149016; PMCID: PMC4712690. (Year: 2015).*
First Office Action issued Jun. 20, 2023 in connection with Japanese Application No. 2020-572381.
First Office Action issued Jul. 3, 2023 in connection with Japanese Application No. 2022-113804.
Office Action and Search Report mailed Jan. 20, 2023 in connection with Russian Patent Application No. 2020142674.
Wang L. et al. Sustained correction of bleeding disorder in hemophilia B mice by gene therapy. Proc. Natl. Acad. Sci. USA, Mar. 30, 1999; 96(7): 3906-3910. doi: 10.1073/pnas.96.7.3906.

(Continued)

*Primary Examiner* — Kade Ariani
(74) *Attorney, Agent, or Firm* — TROUTMAN PEPPER LOCKE LLP

(57) ABSTRACT

Adeno-associated liquid and lyophilized pharmaceutical compositions are provided herein. In exemplary aspects, the pharmaceutical compositions comprise about 5 mM to about 25 mM L-histidine, about 0 mM to about 150 mM sodium chloride, about 0.001% (w/v) to about 0.01% (w/v) polysorbate 80 (PS80), and about 1% to about 10% (w/v) sucrose, trehalose, or combination thereof to AAV. In exemplary aspects, the pharmaceutical compositions further comprise glycine or mannitol. Methods of preparing a pharmaceutical composition comprising AAV, methods of treating a bleeding disorder in a subject, and methods of storing AAV compositions are also provided.

27 Claims, No Drawings

(56) References Cited

FOREIGN PATENT DOCUMENTS

| WO | 2016154055 | 9/2016 |
|---|---|---|
| WO | 20180128689 | 7/2018 |

OTHER PUBLICATIONS

Wright J.F. et al., "Identification of factors that contribute to recombinant AAV2 particle aggregation and tmethods to prevent its occurrence during vectoor purificcation and formulation", Molecular Therapy: The Journal of the American Society of Gene Therapy, Academic Press; Nature Publishing Group, US, vol. 12, No. 1, Jul. 1, 2005, pp. 171-178.

International Preliminary Report on Patentability mailed May 7, 2019 in connection with International Application No. PCT/US17/59971.

International Search Report and Written Opinion mailed Jun. 28, 2018 in connection with PCT/US17/059971.

Office Action mailed Jul. 29, 2021 in connection with Russian Application No. 2019116442.

Monahan, Gene therapy in an era of emerging treatment options for hemophilia B, J. Thromb, Haemost, Jun. 2015: 13 ; S151-S160.

Rayaprolu et al., Comparative analysis of adeno-associated virus capsid stability and dynamics, J. Virol. Dec. 2013; 87(24):13150-160 Epub Sep. 25, 2013.

First Office Action issued Sep. 21, 2021 in connection with Japanese Patent Application No. 2019-522442.

International Search Report and Written Opinion mailed Sep. 27, 2019 in connection with PCT/US19/041398.

International Preliminary Report on Patentability issued Jan. 12, 2021 in connection with PCT/US19/041398.

Decision of Rejection issued Apr. 14, 2022 in connection with JP Application No. 2019-522442.

Supplementary Search Report mailed May 9, 2022 in connection with EP 19833959.0.

Office Action issued Jun. 13, 2023 in connection with. Russian Patent Application No. 2020142674.

Office Action issued Nov. 22, 2021 in connection with U.S. Appl. No. 16/347,107.

Office Action issued Apr. 25, 2024 in connection with U.S. Appl. No. 17/258,516.

Sigma catalogue (www.sigmaaldrich.com/US/en/support/calculators-and-apps/1x-phosphate-buffered-saline, pp. 1-2, year: 2017).

Evans et al. (Journal of Pharmaceutical Science, 93(10), 2458-2375 (Year: 2004).

* cited by examiner

ADENO-ASSOCIATED VIRUS FORMULATIONS

RELATED APPLICATIONS

This application is a continuation from U.S. patent application Ser. No. 16/347,107, filed May 2, 2019, which is a 371 National Stage of PCT/US17/59971, filed Nov. 3, 2017, which claims priority pursuant to 35 U.S.C. § 119(e) to U.S. Provisional Patent Application No. 62/417,750, filed Nov. 4, 2016, which are hereby incorporated by reference in their entirety.

BACKGROUND

Adeno-associated virus (AAV) is a small, non-enveloped virus that packages a linear single-stranded DNA genome. AAV belongs to the family Parvoviridae and the genus Dependovirus, since productive infection by AAV occurs only in the presence of a helper virus, such as, for example, adenovirus or herpes virus. Even in the absence of a helper virus, AAV (serotype 2) can achieve latency by integrating into chromosome 19q13.4 of a host human genome. It is the only mammalian DNA virus known to be capable of site-specific integration (Daya and Berns, Clinical Microbiology Reviews, pages 583-593 (2008)).

For AAV to be safely used in the clinic, AAV has been genetically modified at several locations within its genome. For example, the Rep gene, which is required for viral replication, and the element required for site-specific integration have been eliminated from the AAV genome in many viral vectors. This recombinant AAV (rAAV), exists in an extrachromosomal state and have very low integration efficiency into the genomic DNA. The possibility of rAAV inducing random mutagenesis in a host cell is thus reduced, if not eliminated altogether. Because of these properties and the lack of pathogenicity, rAAV has shown great promise as a gene therapy vector in multiple aspects of pre-clinical and clinical applications. New serotypes and self-complementary vectors are being tested in the clinic. Alongside these ongoing vector developments, continued effort has focused on scalable manufacturing processes that can efficiently generate high titer quantities of rAAV vectors with high purity and potency.

AAV research also has focused on AAV formulations intended for human administration. It is understood that such AAV formulations should be not only safe, sterile, and of good manufacturing practice (GMP) grade, these formulations should also exhibit and promote the long-term stability of the AAV, minimizing loss of AAV potency during the manufacture, packaging, and storage processes. The formulations should furthermore prevent adsorption to the surfaces of the containers in which the AAV are packaged and stored and of the machinery used during manufacture. Though the efforts to design such AAV formulations have been great, there still remains a need for improved AAV formulations.

SUMMARY

The present disclosure provides formulations compatible for human administration which address the unmet needs described above. Advantageously, in some embodiments, the formulations are suitable for long-term storage of AAV, minimizing loss of AAV potency, and advantageously prevent visible particle formation and prevent adsorption to the surfaces of the containers in which the AAV are packaged and stored and of the machinery used during manufacture. In exemplary aspects, the pharmaceutical composition of the present disclosure comprises: adeno-associated virus (AAV) and about 5 mM to about 25 mM of a buffering agent, about 0 mM to about 150 mM of a pharmaceutically acceptable salt, about 0.001% (w/v) to about 0.01% (w/v) of a non-ionic surfactant, and about 1% (w/v) to about 10% (w/v) of a sugar or sugar alcohol. In certain embodiments, the formulation comprises about 50 mM to about 150 mM of a pharmaceutically acceptable salt. In certain embodiments, the formulation comprises about 0 mM to less than about 100 mM of a pharmaceutically acceptable salt. In certain embodiments, the formulation comprises about 30 mM to less than about 100 mM of a pharmaceutically acceptable salt. In certain embodiments, the formulation comprises about 20 mM to about 40 mM of a pharmaceutically acceptable salt.

In exemplary aspects, the pharmaceutical composition of the present disclosure comprises: AAV (e.g., AAV8), about 5 mM to about 25 mM L-histidine, about 0 mM to about 150 mM sodium chloride, about 0.001% (w/v) to about 0.01% (w/v) polysorbate 80 (PS80), and about 1% to about 10% (w/v) sucrose, trehalose, mannitol, or a combination thereof. In certain embodiments, the formulation comprises about 50 mM to about 150 mM sodium chloride. In certain embodiments, the formulation comprises about 0 mM to less than about 100 mM sodium chloride. In certain embodiments, the formulation comprises about 30 mM to less than about 100 mM sodium chloride. In certain embodiments, the formulation comprises about 20 mM to about 40 mM sodium chloride.

In some embodiments, the invention provides a liquid formulation. In certain embodiments, the formulation is lyophilized from a liquid formulation.

In certain aspects, the lyophilized pharmaceutical composition of the present disclosure is lyophilized from a liquid formulation comprising: AAV (e.g., AAV8), about 5 mM to about 25 mM L-histidine, about 0 mM to about 150 mM sodium chloride, about 0.001% (w/v) to about 0.01% (w/v) polysorbate 80 (PS80), about 30 mM to about 70 mM glycine, and about 1% to about 10% (w/v) sucrose, trehalose, mannitol, or a combination thereof. In certain embodiments, the formulation comprises about 50 mM to about 150 mM sodium chloride. In certain embodiments, the formulation comprises about 0 mM to less than about 100 mM sodium chloride. In certain embodiments, the formulation comprises about 30 mM to less than about 100 mM sodium chloride. In certain embodiments, the formulation comprises about 20 mM to about 40 mM sodium chloride.

Methods of preparing a pharmaceutical composition comprising AAV are further provided herein. In exemplary aspects, the method comprises combining about 5 mM to about 25 mM L-histidine, about 0 mM to about 150 mM sodium chloride, about 0.001% (w/v) to about 0.01% (w/v) polysorbate 80 (PS80), about 1% (w/v) to about 10% (w/v) sucrose, trehalose, mannitol, or a combination thereof and AAV, thereby obtaining a pharmaceutical composition comprising AAV. In certain embodiments, the formulation comprises about 50 mM to about 150 mM sodium chloride. In certain embodiments, the formulation comprises about 0 mM to less than about 100 mM sodium chloride. In certain embodiments, the formulation comprises about 30 mM to less than about 100 mM sodium chloride. In certain embodiments, the formulation comprises about 20 mM to about 40 mM sodium chloride.

Methods of treating a subject for a disorder treatable by gene therapy are provided by the present disclosure. In exemplary aspects, the method comprises administering to the subject a pharmaceutical composition as described herein in an amount effective to treat the disorder.

Methods of storing a composition comprising AAV are moreover provided herein. In exemplary aspects, the method comprises combining about 5 mM to about 25 mM L-histidine, about 0 mM to about 150 mM sodium chloride, about 0.001% (w/v) to about 0.01% (w/v) polysorbate 80 (PS80), about 1% (w/v) to about 10% (w/v) sucrose, trehalose, mannitol, or a combination thereof and AAV. In certain embodiments, the formulation comprises about 50 mM to about 150 mM sodium chloride. In certain embodiments, the formulation comprises about 0 mM to less than about 100 mM sodium chloride. In certain embodiments, the formulation comprises about 30 mM to less than about 100 mM sodium chloride. In certain embodiments, the formulation comprises about 20 mM to about 40 mM sodium chloride.

In certain embodiments, the pharmaceutical composition of the present disclosure comprises: AAV and about 20 mM L-histidine, about 70 mM sodium chloride, about 0.005% (w/v) polysorbate 80 (PS80), and about 5% (w/v) sucrose. In some embodiments, the invention provides a liquid formulation. In certain embodiments, the formulation is lyophilized from a liquid formulation.

In certain embodiments, the pharmaceutical composition of the present disclosure comprises: AAV and about 20 mM L-histidine, about 60 mM sodium chloride, about 0.005% (w/v) polysorbate 80 (PS80), about 35 mM trehalose, and about 110 mM mannitol. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 100 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 80 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 70 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 60 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 50 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 40 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 30 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 20 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 10 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

In certain embodiments, the pharmaceutical composition of the present disclosure comprises: AAV and about 10 mM L-histidine, about 0 mM sodium chloride, about 0.005% (w/v) polysorbate 80 (PS80), about 5% (w/v) trehalose, and about 50 mM glycine. In some embodiments, the invention provides a liquid formulation. In certain embodiments, the formulation is lyophilized from a liquid formulation.

Generally, the AAV formulations provided herein are suitable for pharmaceutical administration. In certain embodiments, the AAV is AAV1, AAV2, AAV3, AAV4, AAV5, AAV6, AAV7, AAV8, AAV9, or AAV10. In certain embodiments, the AAV is AAV 2, AAV 5, AAV 8, or AAV 9. In certain embodiments, the AAV is AAV8.

DETAILED DESCRIPTION

The present disclosure provides formulations, e.g., pharmaceutical compositions, compatible for human or veterinarian administration which also are suitable for long-term storage of AAV and minimizing loss of AAV potency. The formulations provided herein are advantageous, because the formulations prevent visible particle formation and also prevent adsorption to the surfaces of the containers in which the AAV are packaged and stored, and prevent adsorption to the machinery used during manufacture. In certain embodiments, the pharmaceutical compositions provided herein retain significant AAV activity when stored for extended periods of time. In certain embodiments, the pharmaceutical compositions provided herein reduce or retard degradation and/or aggregation.

In certain embodiments, the present invention provides formulations of AAV comprising a therapeutically effective amount or dose of an AAV, a sub-physiological to physiological concentration of a pharmaceutically acceptable salt, a stabilizing concentration of one or more sugars and/or sugar alcohols, a non-ionic surfactant, one or more buffering agents providing a neutral pH to the formulation, and optionally an amino acid to aid in stability and recovery of the AAV during purification and/or processing. Generally, the AAV formulations provided herein are suitable for pharmaceutical administration. In certain embodiments, the AAV is AAV8.

In certain embodiments, the composition that contains the AAV is a dehydrated composition. As used herein, a dehydrated composition is a composition that includes water in a low amount, such as 25% or less, or 20% or less, or 15% or less, or 10% or less, or 9% or less, or 8% or less, or 7% or less, or 6% or less, or 5% or less, or 4% or less, or 3% or less, or 2% or less, or 1% or less water as measured by Karl Fischer (KF) titration. In certain embodiments, a dehydrated composition has 3% or less water as measured by Karl Fischer titration. In certain embodiments, a dehydrated composition has 2% or less water as measured by Karl Fischer titration. In certain embodiments, a dehydrated composition has 1% or less water as measured by Karl Fischer titration. In certain embodiments, a dehydrated composition has 0.9% or less water as measured by Karl Fischer titration. In certain embodiments, a dehydrated composition has 0.8% or less water as measured by Karl Fischer titration. In certain embodiments, a dehydrated composition has 0.7% or less water as measured by Karl Fischer titration. In certain embodiments, a dehydrated composition has 0.6% or less water as measured by Karl Fischer titration. In certain embodiments, a dehydrated composition has 0.5% or less water as measured by Karl Fischer titration. In certain embodiments, a dehydrated composition has 0.4% or less water as measured by Karl Fischer titration. In certain embodiments, a dehydrated composition has 0.3% or less water as measured by Karl Fischer titration. In certain embodiments, a dehydrated composition has 0.2% or less water as measured by Karl Fischer titration. Any convenient protocol may be used to produce a dehydrated composition, such as increasing the temperature of the composition (e.g., heating), reducing the pressure, lyophilization (also known as freeze-drying), and the like, and combinations thereof. Other methods for determining the moisture content of the composition includes, but is not limited to, loss of drying (LOD) (measures the amount of water and volatile matters in a sample when the sample is dried under specific conditions), electrolytic sensors (e.g., using a P2O5 sensor), Piezoelectric sorption, oxide sensors, aluminum oxide sensors, absorption spectroscopy, and near infrared (NIR).

Further, it was found that reducing the salt concentration in the lyophilized formulation reduced the residual moisture in the lyocake and assists in the formation of an improved lyocake.

Due to the low water content of a lyophilized composition as described above, the lyophilized composition may be in the form of a solid. In some cases, the solid lyophilized composition is a powder. In some cases, a lyophilized composition may facilitate storage of the composition for an extended period of time (e.g., as compared to a liquid formulation of the same composition). For instance, a lyophilized composition may be a storage stable composition (e.g., a lyophilized storage stable composition), where the composition is substantially stable for an extended period of time. By "stable" or "storage stable" or "substantially stable" is meant a composition that does not significantly degrade and/or lose activity over an extended period of time. For example, a storage stable composition may not have significant impurities due to degradation of the composition over an extended period of time, such as 10% or less impurities, or 9% or less, or 8% or less, or 7% or less, or 6% or less, or 5% or less, or 4% or less, or 3% or less, or 2% or less, or 1% or less degradation products over an extended period of time. In certain instances, a storage stable composition has 5% or less impurities over an extended period of time. In some cases, a storage stable composition substantially retains its activity over an extended period of time, such as retains 100% of its activity, or 99% or more, or 98% or more, or 97% or more, or 96% or more, or 95% or more, or 94% or more, or 93% or more, or 92% or more, or 91% or more, or 90% or more, or 85% or more, or 80% or more, or 75% or more of its activity over an extended period of time. For example, a storage stable composition may retain 90% or more of its activity over an extended period of time. In some cases, a storage stable composition retains 95% or more of its activity over an extended period of time. An extended period of time is a period of time such as 1 week or more, or 2 weeks or more, or 3 weeks or more, or 1 month or more, or 2 months or more, or 3 months or more, or 4 months or more, or 6 months or more, or 9 months or more, or 1 year or more, or 1.5 years (e.g., 18 months) or more, or 2 years or more, or 2.5 years (e.g., 30 months) or more, or 3 years or more, or 3.5 years (e.g., 42 months) or more, or 4 years or more, or 4.5 years (e.g., 54 months) or more, or 5 years or more. For instance, an extended period of time may be 6 months or more. In some cases, an extended period of time is 9 months or more. In some cases, an extended period of time is 1 year (e.g., 12 months) or more. In some cases, an extended period of time is 1.5 years (e.g., 18 months) or more. In some cases, an extended period of time is 2 years (e.g., 24 months) or more. In some embodiments, a storage stable composition is substantially stable for an extended period of time at ambient temperature, such as a temperature of 20 to 40° C., or 25 to 35° C., or 25 to 30° C. In some instances, a storage stable composition is substantially stable for an extended period of time at a temperature less than ambient temperature, such as a temperature of 0 to 20° C., or 0 to 15° C., or 0 to 10° C., or 2 to 8° C.

Definitions

As used herein, the term "AAV" refers to adeno-associated virus in both naturally occurring and recombinant forms (rAAV), and encompasses mutant forms of AAV. The term AAV further includes, but is not limited to, AAV type 1, AAV type 2, AAV type 3, AAV type 4, AAV type 5, AAV type 6, AAV type 7, AAV type 8, AAV type 9, AAV type 10, avian AAV, bovine AAV, canine AAV, equine AAV, ovine AAV, primate AAV, and non-primate AAV. In certain embodiments, the AAV is AAV8.

The phrase "pharmaceutically acceptable," as used in connection with compositions described herein, refers to molecular entities and other ingredients of such compositions that are physiologically tolerable and do not typically produce untoward reactions when administered to a subject. Preferably, the term "pharmaceutically acceptable" means approved by a regulatory agency of the Federal or a state government or listed in the U.S. Pharmacopeia or other generally recognized pharmacopeia for use in mammals, and more particularly in humans. A "pharmaceutically acceptable salt" is a salt that can be formulated into a compound or conjugate for pharmaceutical use including, e.g., metal salts (sodium, potassium, magnesium, calcium, etc.) and salts of ammonia or organic amines that is safe for administration to a subject (e.g., a human) in a drug formulation (see, for example, Berge, et al. "Pharmaceutical Salts," J. Pharm. Sci. 1977; 66:1, which is incorporated herein by reference in its entirety and for all purposes). Suitable "pharmaceutically acceptable salts" include, but are not limited to, metal salts such as sodium, potassium and cesium salts; alkaline earth metal salts such as calcium and magnesium salts; organic amine salts such as triethylamine, guanidine and N-substituted guanidine salts, acetamidine and N-substituted acetamidine, pyridine, picoline, ethanolamine, triethanolamine, dicyclohexylamine, and N,N'-dibenzylethylenediamine salts. "Pharmaceutically acceptable salts" (of basic nitrogen centers) include, but are not limited to inorganic acid salts such as the hydrochloride, hydrobromide, sulfate, phosphate; organic acid salts such as trifluoroacetate and maleate salts; sulfonates such as methanesulfonate, ethanesulfonate, benzenesulfonate, p-toluenesulfonate, camphor sulfonate and naphthalenesulfonate; amino acid salts such as arginate, alaninate, asparaginate and glutamate; and carbohydrate salts such as gluconate and galacturonate. The selection and use of pharmaceutically acceptable salts is well known in the art, for example, see Stahl and Wermuth, Pharmaceutical Salts: Properties, Selection, and Use, 2nd Revised edition, Wiley, Hoboken, N.J., which is incorporated herein by reference in its entirety and for all purposes. Non-limiting examples of pharmaceutically acceptable salts include, without limitation, sodium salts, ammonium salts, potassium salts (e.g, sodium, ammonium, and potassium chloride; sodium, ammonium, and potassium acetate; sodium, ammonium, and potassium citrate; sodium, ammonium, and potassium phosphate; sodium, ammonium, and potassium fluoride; sodium, ammonium, and potassium bromide; and sodium, ammonium, and potassium iodide).

As used herein, a "physiological concentration" of salt refers to a salt concentration of between about 100 mM and about 200 mM of a pharmaceutically acceptable salt.

As used herein, a "sub-physiological concentration" of salt refers to a salt concentration of less than about 100 mM of a pharmaceutically acceptable salt. In certain embodiments, a sub-physiological concentration of salt is less than about 80 mM of a pharmaceutically acceptable salt. In another embodiment, a sub-physiological concentration of salt is less than about 70 mM, less than about 60 mM, less than about 50 mM, less than about 40 mM, less than about 30 mM, less than about 20 mM, or less than about 10 mM of a pharmaceutically acceptable salt.

As used herein, the terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or slowing the development/progression of the disease or a relapse thereof or at least one clinical or sub-clinical symptom thereof; or (3) relieving the disease, i.e., causing regression of the state, disorder or condition or at least one of its clinical or sub-clinical symptoms. As used these terms, do not necessarily imply 100% or complete treatment. Rather, there are varying degrees of treatment of which one of ordinary skill in the art recognizes as having a potential benefit or therapeutic effect. The benefit to a subject to be treated is either statistically significant or at least perceptible to the patient or to the physician. In this respect, the methods of treating a disorder, e.g., a bleeding disorder, of the present disclosure can provide any amount or any level of treatment. Furthermore, the treatment provided by the method of the present disclosure may include treatment of one or more conditions or symptoms or signs of the disorder, being treated.

As used herein, a "therapeutically effective amount or dose" or "sufficient amount or dose" refers to a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The terms "patient" and "subject" are used interchangeably and are used in their conventional sense to refer to a living organism suffering from or prone to a condition that can be prevented or treated by administration of a composition of the present disclosure, and includes both humans and non-human animals. Examples of subjects include, but are not limited to, humans, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, adult, juvenile and newborn individuals are of interest.

As used herein, "storage" means that a formulation is not immediately administered to a subject once prepared, but is kept for a period of time under particular conditions (e.g. particular temperature, etc.) prior to use. For example, a liquid or lyophilized formulation can be kept for days, weeks, months or years, prior to administration to a subject under varied temperatures such as refrigerated (0° to 10° C.) or room temperature (e.g., temperature up to 32° C.).

As used herein, the term "about" denotes an approximate range of plus or minus 10% from a specified value. For instance, the language "about 20%" encompasses a range of 18-22%. As used herein, about also includes the exact amount. Hence "about 20%" means "about 20%" and also "20%.

As used herein, the term "and/or" refers to and encompasses any and all possible combinations of one or more of the associated listed items, as well as the lack of combinations when interpreted in the alternative ("or").

As used herein, the term "or" refers to any one member of a particular list and also includes any combination of members of that list.

As used herein, the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

AAV Compositions and Formulations

In exemplary aspects, the pharmaceutical composition of the present disclosure comprises: adeno-associated virus (AAV) and about 5 mM to about 25 mM of a buffering agent, about 0 mM to about 150 mM of a pharmaceutically acceptable salt, about 0.001% (w/v) to about 0.01% (w/v) of a non-ionic surfactant, and about 1% (w/v) to about 10% (w/v) of a sugar or sugar alcohol.

In exemplary aspects, the pharmaceutical composition of the present disclosure comprises: adeno-associated virus (AAV) and about 5 mM to about 25 mM of a buffering agent, about 50 mM to about 150 mM of a pharmaceutically acceptable salt, about 0.001% (w/v) to about 0.01% (w/v) of a non-ionic surfactant, and about 1% (w/v) to about 10% (w/v) of a sugar or sugar alcohol.

In exemplary aspects, the pharmaceutical composition of the present disclosure comprises: adeno-associated virus (AAV) and about 5 mM to about 25 mM of a buffering agent, about 0 mM to less than 100 mM of a pharmaceutically acceptable salt, about 0.001% (w/v) to about 0.01% (w/v) of a non-ionic surfactant, and about 1% (w/v) to about 10% (w/v) of a sugar or sugar alcohol.

In exemplary aspects, the pharmaceutical composition of the present disclosure comprises: adeno-associated virus (AAV) and about 5 mM to about 25 mM of a buffering agent, about 30 mM to less than 100 mM of a pharmaceutically acceptable salt, about 0.001% (w/v) to about 0.01% (w/v) of a non-ionic surfactant, and about 1% (w/v) to about 10% (w/v) of a sugar or sugar alcohol.

In certain instances, the composition is a sterile composition. By "sterile" is meant that there are substantially no immunogenic components in the composition, such as for example substantially no microbes (e.g., fungi, bacteria, viruses, spore forms, etc.).

In some embodiments, the invention provides a liquid formulation. In certain embodiments, the formulation is lyophilized from a liquid formulation.

In exemplary aspects, the pharmaceutical composition of the present disclosure comprises about 5 mM to about 25 mM, about 5 mM to about 15 mM, about 10 mM to about 20 mM, or about 15 mM to about 25 mM of a buffering agent. In exemplary aspects, the pharmaceutical composition comprises about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, or about 25 mM of a buffering agent.

Pharmaceutically acceptable buffering agents are well known in the art, and include without limitation, phosphate buffers, histidine, sodium citrate, HEPES, Tris, Bicine, glycine, N-glycylglycine, sodium acetate, sodium carbonate, glycyl glycine, lysine, arginine, sodium phosphate, and mixtures thereof. In certain embodiments, the buffer is histidine (e.g., L-histidine).

In exemplary aspects, the pharmaceutical composition of the present disclosure comprises about 5 mM to about 25 mM, about 5 mM to about 15 mM, about 10 mM to about 20 mM, or about 15 mM to about 25 mM L-histidine. In exemplary aspects, the pharmaceutical composition comprises about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, or about 25 mM L-histidine. In certain embodiments, the pharmaceutical composition comprises about 10 mM L-histidine. In certain embodiments, the pharmaceutical composition comprises about 20 mM L-histidine.

In exemplary aspects, the pharmaceutical composition of the present disclosure comprises about 0 mM to about 150 mM, about 5 mM to about 150 mM, about 5 mM to about 100 mM, about 5 mM to about 90 mM, about 5 mM to about 80 mM, about 5 mM to about 70 mM, about 5 mM to about 60 mM, about 5 mM to about 50 mM, about 5 mM to about 40 mM, 5 mM to about 30 mM, about 30 mM to about 100 mM, about 30 mM to about 90 mM, about 30 mM to about 80 mM, about 30 mM to about 70 mM, about 30 mM to about 60 mM, about 30 mM to about 50 mM, about 30 mM to about 40 mM, about 50 mM to about 150 mM, 50 mM to about 120 mM, about 55 mM to about 100 mM, about 60 mM to about 100 mM, about 60 mM to about 80 mM, about 70 mM to about 100 mM, or about 70 mM to about 80 mM of a pharmaceutically acceptable salt (as defined above). In certain embodiments, the pharmaceutical composition of the present disclosure comprises about 80 mM to about 120 mM, about 70 mM to about 90 mM, about 50 mM to about 70 mM, or about 20 mM to about 40 mM of a pharmaceutically acceptable salt. In exemplary aspects, the pharmaceutical composition of the present disclosure comprises about 0 mM to about 100 mM, about 0 mM to about 80 mM, about 0 mM to about 70 mM, about 0 mM to about 60 mM, about 0 mM to about 50 mM, about 0 mM to about 40 mM, about 0 mM to about 30 mM, about 0 mM to about 20 mM, about 0 mM to about 10 mM, about 0 mM to about 5 mM of a pharmaceutically acceptable salt. In exemplary aspects, the pharmaceutical composition comprises about 0 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, or about 150 mM of a pharmaceutically acceptable salt. In other embodiments, the pharmaceutical composition comprises about 0 mM to less than about 100 mM, about 5 mM to less than about 100 mM, about 10 mM to less than about 100 mM, about 20 mM to less than about 100 mM, about 30 mM to less than about 100 mM, about 40 mM to less than about 100 mM, about 50 mM to less than about 100 mM, about 60 mM to less than about 100 mM, or about 70 mM to less than about 100 mM of a pharmaceutically acceptable salt. In certain embodiments, the pharmaceutical composition of the present disclosure comprises about 0 mM of a pharmaceutically acceptable salt. In certain embodiments, the pharmaceutical composition of the present disclosure comprises about 30 mM of a pharmaceutically acceptable salt. In certain embodiments, the pharmaceutical composition of the present disclosure comprises about 40 mM of a pharmaceutically acceptable salt. In certain embodiments, the pharmaceutical composition of the present disclosure comprises about 50 mM of a pharmaceutically acceptable salt. In certain embodiments, the pharmaceutical composition of the present disclosure comprises about 60 mM of a pharmaceutically acceptable salt. In certain embodiments, the pharmaceutical composition of the present disclosure comprises about 70 mM of a pharmaceutically acceptable salt. In certain embodiments, the pharmaceutical composition of the present disclosure comprises about 80 mM of a pharmaceutically acceptable salt. In certain embodiments, the pharmaceutical composition of the present disclosure comprises about 100 mM of a pharmaceutically acceptable salt. In certain embodiments, the pharmaceutically acceptable salt is a sodium salt (e.g., sodium chloride).

Advantageously, it has been found that pharmaceutical compositions containing a sub-physiological concentration of a pharmaceutically acceptable salt forms compact lyocakes with lower moisture content and assists in the formation of an improved lyocake. In certain embodiments, the sub-physiological concentration of the pharmaceutically acceptable salt results in white, compact and homogenous lyocakes. Accordingly, in certain embodiments, the present disclosure provides low salt pharmaceutical compositions containing a sub-physiological concentration of a pharmaceutically acceptable salt, for example, less than about 100 mM of a pharmaceutically acceptable salt. In one embodiment, a low salt formulation provided herein contains less than about 100 mM of a pharmaceutical salt. In certain embodiments, a low salt pharmaceutical composition provided herein contains less than about 80 mM of a pharmaceutical salt. In certain embodiments, a low salt pharmaceutical composition provided herein contains less than about 70 mM of a pharmaceutical salt. In another embodiment, a low salt pharmaceutical composition provided herein contains less than about 60 mM of a pharmaceutical salt. In another embodiment, a low salt pharmaceutical composition provided herein contains less than about 50 mM of a pharmaceutical salt. In another embodiment, a low salt pharmaceutical composition provided herein contains less than about 40 mM of a pharmaceutical salt. In another embodiment, a low salt pharmaceutical composition provided herein contains less than about 30 mM of a pharmaceutical salt. In another embodiment, a low salt pharmaceutical composition provided herein contains less than about 20 mM of a pharmaceutical salt. In another embodiment, a low salt pharmaceutical composition provided herein contains less than about 10 mM of a pharmaceutical salt. In another embodiment, a low salt pharmaceutical composition contains between about 30 mM and about 60 mM of a pharmaceutically acceptable salt. In yet other embodiments, a low salt pharmaceutical composition contains about 0 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM of a pharmaceutically acceptable salt. In certain embodiments, the pharmaceutical composition of the present disclosure comprises about 0 mM of a pharmaceutically acceptable salt. In certain embodiments, the pharmaceutical composition of the present disclosure comprises about 30 mM of a pharmaceutically acceptable salt. In certain embodiments, the pharmaceutical composition of the present disclosure comprises about 40 mM of a pharmaceutically acceptable salt. In certain embodiments, the pharmaceutical composition of the present disclosure comprises about 50 mM of a pharmaceutically acceptable salt. In certain embodiments, the pharmaceutical composition of the present disclosure comprises about 60 mM of a pharmaceutically acceptable salt. In certain embodiments, the pharmaceutical composition of the present disclosure comprises about 70 mM of a pharmaceutically acceptable salt. In certain embodiments, the pharmaceutical composition of the present disclosure comprises about 80 mM of a pharmaceutically acceptable salt. In a preferred embodiment, a low salt pharmaceutical composition is a lyophilized formulation. In a preferred embodiment, the salt is a sodium salt (e.g., sodium chloride).

In exemplary aspects, the pharmaceutical composition of the present disclosure comprises about 0 mM to about 150 mM, about 5 mM to about 150 mM, about 5 mM to about 100 mM, about 5 mM to about 90 mM, about 5 mM to about 80 mM, about 5 mM to about 70 mM, about 5 mM to about 60 mM, about 5 mM to about 50 mM, about 5 mM to about 40 mM, 5 mM to about 30 mM, about 30 mM to about 100 mM, about 30 mM to about 90 mM, about 30 mM to about 80 mM, about 30 mM to about 70 mM, about 30 mM to about 60 mM, about 30 mM to about 50 mM, about 30 mM to about 40 mM, about 50 mM to about 150 mM, 50 mM to about 120 mM, about 55 mM to about 100 mM, about 60 mM to about 100 mM, about 60 mM to about 80 mM, about 70 mM to about 100 mM, or about 70 mM to about 80 mM sodium chloride. In certain embodiments, the pharmaceutical composition of the present disclosure comprises about 80 mM to about 120 mM, about 70 mM to about 90 mM, about 50 mM to about 70 mM, or about 20 mM to about 40 mM sodium chloride. In exemplary aspects, the pharmaceutical composition of the present disclosure comprises about 0 mM to about 100 mM, about 0 mM to about 80 mM, about 0 mM to about 70 mM, about 0 mM to about 60 mM, about 0 mM to about 50 mM, about 0 mM to about 40 mM, about 0 mM to about 30 mM, about 0 mM to about 20 mM, about 0 mM to about 10 mM, about 0 mM to about 5 mM sodium chloride. In certain embodiments, the pharmaceutical composition comprises less than about 100 mM, less than about 80 mM, less than about 70 mM, or less than about 60 mM sodium chloride. In other embodiments, the pharmaceutical composition comprises about 0 mM to less than about 100 mM, about 5 mM to less than about 100 mM, about 10 mM to less than about 100 mM, about 20 mM to less than about 100 mM, about 30 mM to less than about 100 mM, about 40 mM to less than about 100 mM, about 50 mM to less than about 100 mM, about 60 mM to less than about 100 mM, or about 70 mM to less than about 100 mM sodium chloride. In exemplary aspects, the pharmaceutical composition comprises about 0 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, or about 150 mM sodium chloride. In certain embodiments, the pharmaceutical composition of the present disclosure comprises about 0 mM sodium chloride. In certain embodiments, the pharmaceutical composition of the present disclosure comprises about 10 mM sodium chloride. In certain embodiments, the pharmaceutical composition of the present disclosure comprises about 20 mM sodium chloride. In certain embodiments, the pharmaceutical composition of the present disclosure comprises about 30 mM sodium chloride. In certain embodiments, the pharmaceutical composition of the present disclosure comprises about 40 mM sodium chloride. In certain embodiments, the pharmaceutical composition of the present disclosure comprises about 50 mM sodium chloride. In certain embodiments, the pharmaceutical composition of the present disclosure comprises about 60 mM sodium chloride. In certain embodiments, the pharmaceutical composition of the present disclosure comprises about 70 mM sodium chloride. In certain embodiments, the pharmaceutical composition of the present disclosure comprises about 80 mM sodium chloride. In certain embodiments, the pharmaceutical composition of the present disclosure comprises about 100 mM sodium chloride.

Advantageously, it was also found that the inclusion of a non-ionic surfactant substantially reduces the loss of AAV on surfaces and prevents formation of visible particles of the pharmaceutical compositions. Accordingly, in certain embodiments, pharmaceutical compositions containing a stabilizing concentration of a non-ionic detergent are provided. Pharmaceutically acceptable non-ionic surfactants that may be used in the formulations disclosed herein are known in the art of pharmaceutical science, and include, without limitation, Polysorbate 80 (Tween 80; PS80), Polysorbate 20 (Tween 20; PS20), and various poloxamers or pluronics, including Pluronic F-68, and BRIJ 35, or mixtures thereof. In a preferred embodiment, the non-ionic surfactant used in the present pharmaceutical compositions is Polysorbate 80. In exemplary aspects, the pharmaceutical composition of the present disclosure comprises Super Refined™ PS80 commercially available from Croda Health Care (Snaith, UK).

In certain embodiments, the pharmaceutical composition of the present disclosure comprises about 0.001% (w/v) to about 0.01% (w/v) or about 0.0025% (w/v) to about 0.0075% (w/v) non-ionic surfactant. In exemplary aspects, the pharmaceutical composition comprises about 0.001% (w/v), about 0.0015% (w/v), about 0.002% (w/v), about 0.0025% (w/v), about 0.003% (w/v), about 0.0035% (w/v), about 0.004% (w/v), about 0.0045% (w/v), about 0.005% (w/v), about 0.0055% (w/v), about 0.006% (w/v), about 0.0065% (w/v), about 0.007% (w/v), about 0.0075% (w/v), about 0.008% (w/v), about 0.0085% (w/v), about 0.009% (w/v), about 0.0095% (w/v), about 0.001% (w/v) non-ionic surfactant. In certain embodiments, the pharmaceutical composition of the present disclosure comprises about 0.005% (w/v) non-ionic surfactant.

In exemplary aspects, the pharmaceutical composition of the present disclosure comprises about 0.001% (w/v) to about 0.01% (w/v) or about 0.0025% (w/v) to about 0.0075% (w/v) polysorbate 80 (e.g., Super Refined™ PS80). In exemplary aspects, the pharmaceutical composition comprises about 0.001% (w/v), about 0.0015% (w/v), about 0.002% (w/v), about 0.0025% (w/v), about 0.003% (w/v), about 0.0035% (w/v), about 0.004% (w/v), about 0.0045% (w/v), about 0.005% (w/v), about 0.0055% (w/v), about 0.006% (w/v), about 0.0065% (w/v), about 0.007% (w/v), about 0.0075% (w/v), about 0.008% (w/v), about 0.0085% (w/v), about 0.009% (w/v), about 0.0095% (w/v), about 0.001% (w/v) PS80. In certain embodiments, the pharmaceutical composition of the present disclosure comprises about 0.005% (w/v) PS80.

It was found that the inclusion of moderate levels (i.e., between about 1% to about 10%) of one or more sugar and/or sugar alcohol assists in the stability of the liquid and/or lyophilized formulations. For example, the sugar and/or sugar alcohol allows for better properties during freeze/thawing cycles. Accordingly, in certain embodiments, the present invention provides pharmaceutical compositions containing between about 2% and about 10% of one or more sugars and/or sugar alcohols. Any sugar such as mono-, di-, or polysaccharides, or water-soluble glucans, including for example fructose, glucose, mannose, sorbose, xylose, maltose, lactose, sucrose, dextran, trehalose, pullulan, dextrin, cyclodextrin, soluble starch, hydroxyethyl starch, and carboxymethylcellulose may be used. In a particular embodiment, the sugar is sucrose, trehalose, or a combination thereof. In certain embodiments, the trehalose is trehalose dihydrate. Sugar alcohols are defined as a hydrocarbon having between about 4 and about 8 carbon atoms and a hydroxyl group. Non-limiting examples of sugar alcohols that may be used in the pharmaceutical compositions provided herein include, mannitol, sorbitol, inositol, galactitol, dulcitol, xylitol, and arabitol. In certain embodiments, mannitol is used as a sugar alcohol additive. In certain embodiments, a pharmaceutical composition contains both a sugar and a sugar alcohol additive.

The sugars and sugar alcohols may be used individually or in combination. In some embodiments, the sugar, sugar alcohol, or combination thereof will be present in the formulation at a concentration of about 1% to about 10% (w/v), about 1% (w/v) to about 1.5% (w/v), about 2.5% to about 7.5% (w/v), or about 1% to about 5% (w/v). In exemplary aspects, the pharmaceutical composition of the present disclosure comprises about 1.0% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2.0% (w/v), about 2.5% (w/v), about 3.0% (w/v), about 3.5% (w/v), about 4.0% (w/v), about 4.5% (w/v), about 5.0% (w/v), about 5.5% (w/v), about 6.0% (w/v), about 6.5% (w/v), about 7.0% (w/v), about 7.5% (w/v), about 8.0% (w/v), about 8.5% (w/v), about 9.0% (w/v), about 9.5% (w/v), or about 10% (w/v) sugar, sugar alcohol, or combination thereof. In certain embodiments, the sugar is sucrose, trehalose, or a combination thereof. In certain embodiments, the trehalose is trehalose dihydrate.

In certain embodiments, the pharmaceutical composition of the present disclosure comprises about 1% to about 10% (w/v), about 1% (w/v) to about 1.5% (w/v), about 2.5% to about 7.5% (w/v), or about 1% to about 5% (w/v) sucrose, trehalose, or a combination thereof. In exemplary aspects, the pharmaceutical composition of the present disclosure comprises about 1.0% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2.0% (w/v), about 2.5% (w/v), about 3.0% (w/v), about 3.5% (w/v), about 4.0% (w/v), about 4.5% (w/v), about 5.0% (w/v), about 5.5% (w/v), about 6.0% (w/v), about 6.5% (w/v), about 7.0% (w/v), about 7.5% (w/v), about 8.0% (w/v), about 8.5% (w/v), about 9.0% (w/v), about 9.5% (w/v), or about 10% (w/v) sucrose, trehalose, or a combination thereof. In certain embodiments, the pharmaceutical composition of the present disclosure comprises about 1.3% (w/v) sucrose, trehalose, or a combination thereof. In certain embodiments, the pharmaceutical composition of the present disclosure comprises about 5% (w/v) sucrose, trehalose, or a combination thereof. In exemplary aspects, the pharmaceutical composition of the present disclosure comprises 10 mM to about 150 mM, about 30 mM to about 40 mM, or about 35 mM to about 132 mM sucrose, trehalose, or a combination thereof. In exemplary aspects, the pharmaceutical composition of the present disclosure comprises about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 110 mM, about 120 mM, about 130 mM, about 140 mM, or about 150 mM sucrose, trehalose, or a combination thereof. In certain embodiments, the pharmaceutical composition of the present disclosure comprises about 35 mM sucrose, trehalose, or a combination thereof. In certain embodiments, the pharmaceutical composition of the present disclosure comprises about 132 mM sucrose, trehalose, or a combination thereof. In exemplary aspects, the trehalose is trehalose dihydrate.

In exemplary aspects, the pharmaceutical composition of the present disclosure comprises: adeno-associated virus (AAV) and about 5 mM to about 25 mM L-histidine, about 0 mM to about 150 mM pharmaceutically acceptable salt, about 0.001% (w/v) to about 0.01% (w/v) non-ionic surfactant, and about 1% (w/v) to about 10% (w/v) sugar and/or sugar alcohol. In certain embodiments, the pharmaceutically acceptable salt is about 0 nM to about 100 mM. In certain embodiments, the pharmaceutically acceptable salt is about 30 nM to about 100 mM. In certain embodiments, the pharmaceutically acceptable salt is about 5 nM to about 150 mM. In certain embodiments, the pharmaceutically acceptable salt is about 50 nM to about 150 mM. In certain embodiments, the pharmaceutically acceptable salt is sodium chloride.

In exemplary aspects, the pharmaceutical composition of the present disclosure further comprises glycine. In exemplary aspects, the pharmaceutical composition of the present disclosure comprises about 30 mM to about 70 mM, about 35 mM to about 65 mM glycine, about 40 mM to about 60 mM, or about 45 mM to about 55 mM glycine. In exemplary aspects, the pharmaceutical composition of the present disclosure comprises about 30 mM, about 35 mM, about 40 mM, about 45 mM, about 50 mM, about 55 mM, about 60 mM, about 65 mM, or about 70 mM glycine. In certain embodiments, the pharmaceutical composition of the present disclosure further comprises about 50 mM glycine.

In exemplary aspects, the pharmaceutical composition of the present disclosure further comprises mannitol. In exemplary aspects, the pharmaceutical composition of the present disclosure comprises about 50 mM to about 150 mM, about 60 mM to about 140 mM, about 70 mM to about 130 mM, about 80 mM to about 120 mM, or about 90 mM to about 110 mM mannitol. In certain embodiments, the pharmaceutical composition of the present disclosure comprises about 110 mM mannitol. In exemplary aspects, the pharmaceutical composition of the present disclosure comprises glycine or mannitol, but not both glycine and mannitol.

In other embodiments, the pharmaceutical composition of the present disclosure comprises: adeno-associated virus (AAV) and about 5 mM to about 25 mM L-histidine, about 0 mM to about 150 mM pharmaceutically acceptable salt, about 0.001% (w/v) to about 0.01% (w/v) non-ionic surfactant, and about 1% (w/v) to about 10% (w/v) sugar and/or sugar alcohol. In certain embodiments, the pharmaceutically acceptable salt is about 0 nM to about 100 mM. In certain embodiments, the pharmaceutically acceptable salt is about 30 nM to about 100 mM. In certain embodiments, the pharmaceutically acceptable salt is about 5 nM to about 150 mM. In certain embodiments, the pharmaceutically acceptable salt is about 50 nM to about 150 mM. certain embodiments, the sugar and/or sugar alcohol is sucrose, trehalose, mannitol, and a combination thereof. In certain embodiments, the pharmaceutically acceptable salt is sodium chloride.

In other embodiments, the pharmaceutical composition of the present disclosure comprises: adeno-associated virus (AAV) and about 5 mM to about 25 mM L-histidine, about 0 mM to about 150 mM pharmaceutically acceptable salt, about 0.001% (w/v) to about 0.01% (w/v) non-ionic surfactant, and about 1% (w/v) to about 10% (w/v) sugar and/or sugar alcohol. In certain embodiments, the pharmaceutically acceptable salt is about 0 nM to about 100 mM. In certain embodiments, the pharmaceutically acceptable salt is about 30 nM to about 100 mM. In certain embodiments, the pharmaceutically acceptable salt is about 5 nM to about 150 mM. In certain embodiments, the pharmaceutically acceptable salt is about 50 nM to about 150 mM. In certain embodiments, the non-ionic surfactant is Polysorbate 20, Polysorbate 80, Pluronic F-68, BRIJ 35, and a combination thereof. In certain embodiments, the sugar and/or sugar alcohol is sucrose, trehalose, mannitol, and a combination thereof. In certain embodiments, the non-ionic surfactant is PS80. In certain embodiments, the pharmaceutically acceptable salt is sodium chloride.

In exemplary aspects, the pharmaceutical composition of the present disclosure comprises: adeno-associated virus (AAV) and about 5 mM to about 25 mM L-histidine, less than about 100 mM pharmaceutically acceptable salt, about 0.001% (w/v) to about 0.01% (w/v) non-ionic surfactant, and about 1% (w/v) to about 10% (w/v) sugar and/or sugar alcohol. In certain embodiments, the pharmaceutically acceptable salt is about 0 nM to less than about 100 mM. In certain embodiments, the pharmaceutically acceptable salt is about 0 nM to about 80 mM, about 0 nM to about 70 mM, about 0 mM to about 60 mM, about 0 mM to about 50 mM, about 0 mM to about 40 mM, 0 mM to about 30 mM, about 0 mM to about 20 mM, or 0 mM to about 10 mM. In certain embodiments, the pharmaceutically acceptable salt is about 30 nM to less than about 100 mM. In certain embodiments, the pharmaceutically acceptable salt is about 30 nM to about 80 mM, about 30 nM to about 70 mM, about 30 mM to about 60 mM, about 30 mM to about 50 mM, or about 30 mM to about 40 mM. In certain embodiments, the pharmaceutically acceptable salt is sodium chloride. In certain embodiments, the pharmaceutical composition of the present disclosure comprises glycine or mannitol, but not both glycine and/or mannitol. In certain embodiments, the pharmaceutical composition of the present disclosure comprises glycine or mannitol, but not both glycine and mannitol. In certain embodiments, the formulation is a liquid formulation. In certain embodiments, the formulation is a lyophilized formulation. In certain embodiments, the lower salt pharmaceutical composition is a lyophilized formulation.

In other embodiments, the pharmaceutical composition of the present disclosure comprises: adeno-associated virus (AAV) and about 5 mM to about 25 mM L-histidine, less than about 100 mM pharmaceutically acceptable salt, about 0.001% (w/v) to about 0.01% (w/v) non-ionic surfactant, and about 1% (w/v) to about 10% (w/v) sugar and/or sugar alcohol. In certain embodiments, the pharmaceutically acceptable salt is about 0 nM to less than about 100 mM. In certain embodiments, the pharmaceutically acceptable salt is about 0 nM to about 80 mM, about 0 nM to about 70 mM, about 0 mM to about 60 mM, about 0 mM to about 50 mM, about 0 mM to about 40 mM, 0 mM to about 30 mM, about 0 mM to about 20 mM, or 0 mM to about 10 mM. In certain embodiments, the pharmaceutically acceptable salt is about 30 nM to less than about 100 mM. In certain embodiments, the pharmaceutically acceptable salt is about 30 nM to about 80 mM, about 30 nM to about 70 mM, about 30 mM to about 60 mM, about 30 mM to about 50 mM, or about 30 mM to about 40 mM. In certain embodiments, the sugar and/or sugar alcohol is sucrose, trehalose, mannitol, and a combination thereof. In certain embodiments, the pharmaceutically acceptable salt is sodium chloride. In certain embodiments, the formulation is a liquid formulation. In certain embodiments, the formulation is a lyophilized formulation. In certain embodiments, the lower salt pharmaceutical composition is a lyophilized formulation.

In other embodiments, the pharmaceutical composition of the present disclosure comprises: adeno-associated virus (AAV) and about 5 mM to about 25 mM L-histidine, less than about 100 mM pharmaceutically acceptable salt, about 0.001% (w/v) to about 0.01% (w/v) non-ionic surfactant, and about 1% (w/v) to about 10% (w/v) sugar and/or sugar alcohol. In certain embodiments, the pharmaceutically acceptable salt is about 0 nM to less than about 100 mM. In certain embodiments, the pharmaceutically acceptable salt is about 0 nM to about 80 mM, about 0 nM to about 70 mM, about 0 mM to about 60 mM, about 0 mM to about 50 mM, about 0 mM to about 40 mM, 0 mM to about 30 mM, about 0 mM to about 20 mM, or 0 mM to about 10 mM. In certain embodiments, the pharmaceutically acceptable salt is about 30 nM to less than about 100 mM. In certain embodiments, the pharmaceutically acceptable salt is about 30 nM to about 80 mM, about 30 nM to about 70 mM, about 30 mM to about 60 mM, about 30 mM to about 50 mM, or about 30 mM to about 40 mM. In certain embodiments, the non-ionic surfactant is Polysorbate 20, Polysorbate 80, Pluronic F-68, BRIJ 35, and a combination thereof. In certain embodiments, the sugar and/or sugar alcohol is sucrose, trehalose, mannitol, and a combination thereof. In certain embodiments, the non-ionic surfactant is PS80. In certain embodiments, the pharmaceutically acceptable salt is sodium chloride. In certain embodiments, the formulation is a liquid formulation. In certain embodiments, the formulation is a lyophilized formulation. In certain embodiments, the lower salt pharmaceutical composition is a lyophilized formulation.

In exemplary aspects, the pharmaceutical composition of the present disclosure comprises: adeno-associated virus (AAV) and about 5 mM to about 25 mM L-histidine, about 50 mM to about 150 mM sodium chloride, about 0.001% (w/v) to about 0.01% (w/v) polysorbate 80 (PS80), and about 1% (w/v) to about 10% (w/v) sucrose or trehalose.

In exemplary aspects, the pharmaceutical composition of the present disclosure comprises: adeno-associated virus (AAV) and about 5 mM to about 25 mM L-histidine, about 0 mM to less than about 100 mM sodium chloride, about 0.001% (w/v) to about 0.01% (w/v) polysorbate 80 (PS80), and about 1% (w/v) to about 10% (w/v) sucrose or trehalose. In certain embodiments, the formulation is a liquid formulation. In certain embodiments, the formulation is a lyophilized formulation. In certain embodiments, the lower salt pharmaceutical composition is a lyophilized formulation.

In exemplary aspects, the pharmaceutical composition of the present disclosure comprises: adeno-associated virus (AAV) and about 5 mM to about 25 mM L-histidine, about 30 mM to about 80 mM sodium chloride, about 0.001% (w/v) to about 0.01% (w/v) polysorbate 80 (PS80), and about 1% (w/v) to about 10% (w/v) sucrose or trehalose. In certain embodiments, the formulation is a liquid formulation. In certain embodiments, the formulation is a lyophilized formulation. In certain embodiments, the lower salt pharmaceutical composition is a lyophilized formulation.

In certain embodiments, lower salt pharmaceutical compositions are provided comprising adeno-associated virus (AAV) and about 5 mM to about 25 mM L-histidine, about 50 mM to about 150 mM sodium chloride, about 0.001% (w/v) to about 0.01% (w/v) polysorbate 80 (PS80), and about 1% (w/v) to about 10% (w/v) sucrose or trehalose. In certain embodiments, the pharmaceutical composition of the present disclosure further comprises about 30 mM to about 70 mM glycine. In certain embodiments, the formulation is a liquid formulation. In certain embodiments, the formulation is a lyophilized formulation. In certain embodiments, the lower salt pharmaceutical composition is a lyophilized formulation.

In certain embodiments, lower salt pharmaceutical compositions are provided comprising adeno-associated virus (AAV) and about 5 mM to about 25 mM L-histidine, about 0 mM to less than about 100 mM sodium chloride, about 0.001% (w/v) to about 0.01% (w/v) polysorbate 80 (PS80), and about 1% (w/v) to about 10% (w/v) sucrose or trehalose. In certain embodiments, the pharmaceutical composition of the present disclosure further comprises about 30 mM to about 70 mM glycine. In certain embodiments, the pharmaceutical composition comprises less than about 80 mM sodium chloride. In certain embodiments, the pharmaceutical composition comprises less than about 70 mM sodium chloride. In certain embodiments, the pharmaceutical composition comprises less than about 60 mM sodium chloride. In certain embodiments, the pharmaceutical composition comprises less than about 50 mM sodium chloride. In certain embodiments, the pharmaceutical composition comprises less than about 40 mM sodium chloride. In certain embodiments, the pharmaceutical composition comprises less than about 30 mM sodium chloride. In certain embodiments, the pharmaceutical composition comprises about 0 mM to about 80 mM sodium chloride. In certain embodiments, the pharmaceutical composition comprises about 0 mM to about 70 mM sodium chloride. In certain embodiments, the pharmaceutical composition comprises about 0 mM to about 60 mM sodium chloride. In certain embodiments, the pharmaceutical composition comprises about 0 mM to about 50 mM sodium chloride. In certain embodiments, the pharmaceutical composition comprises about 0 mM to about 40 mM sodium chloride. In certain embodiments, the pharmaceutical composition comprises about 0 mM to about 30 mM sodium chloride. In certain embodiments, the pharmaceutical composition comprises about 30 mM to about 80 mM sodium chloride. In certain embodiments, the pharmaceutical composition comprises about 30 mM to about 70 mM sodium chloride. In certain embodiments, the pharmaceutical composition comprises about 30 mM to about 60 mM sodium chloride. In certain embodiments, the pharmaceutical composition comprises about 30 mM to about 50 mM sodium chloride. In certain embodiments, the pharmaceutical composition comprises about 30 mM to about 40 mM sodium chloride. In certain embodiments, the formulation is a liquid formulation. In certain embodiments, the formulation is a lyophilized formulation. In certain embodiments, the lower salt pharmaceutical composition is a lyophilized formulation.

The present disclosure also provides a pharmaceutical composition comprising adeno-associated virus (AAV) and about 20 mM L-histidine, about 70 mM sodium chloride, about 0.005% (w/v) polysorbate 80 (PS80), and about 5% (w/v) sucrose. In certain embodiments, the pH of the pharmaceutical composition is about 7.5±0.2 and/or the osmolality is about 300±10 mOsmol/kg.

The present disclosure further provides a pharmaceutical composition comprising adeno-associated virus (AAV) and about 20 mM L-histidine, about 60 mM sodium chloride, about 0.005% (w/v) polysorbate 80 (PS80), about 35 mM trehalose, and about 110 mM mannitol. In certain embodiments, the pH of the pharmaceutical composition is about 7.0±0.2 and/or the osmolality is about 390±10 mOsmol/kg. In certain embodiments, the pH of the pharmaceutical composition is about 7.0±0.2 and/or the osmolality is about 290±10 mOsmol/kg.

The present disclosure further provides a pharmaceutical composition comprising adeno-associated virus (AAV) and about 10 mM L-histidine, about 100 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2 and/or the osmolality is about 400±10 mOsmol/kg.

The present disclosure further provides a pharmaceutical composition that can be liquid or lyophilized (e.g., lyophilized from a liquid formulation) comprising adeno-associated virus (AAV) and about 10 mM L-histidine, about 80 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2.

The present disclosure further provides a pharmaceutical composition that can be liquid or lyophilized (e.g., lyophilized from a liquid formulation) comprising adeno-associated virus (AAV) and about 10 mM L-histidine, about 70 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2.

The present disclosure further provides a pharmaceutical composition that can be liquid or lyophilized (e.g., lyophilized from a liquid formulation) comprising adeno-associated virus (AAV) and about 10 mM L-histidine, about 60 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2.

The present disclosure further provides a pharmaceutical composition that can be liquid or lyophilized (e.g., lyophilized from a liquid formulation) comprising adeno-associated virus (AAV) and about 10 mM L-histidine, about 50 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2.

The present disclosure further provides a pharmaceutical composition that can be liquid or lyophilized (e.g., lyophilized from a liquid formulation) comprising adeno-associated virus (AAV) and about 10 mM L-histidine, about 40 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2.

The present disclosure further provides a pharmaceutical composition that can be liquid or lyophilized (e.g., lyophilized from a liquid formulation) comprising adeno-associated virus (AAV) and about 10 mM L-histidine, about 30 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2.

The present disclosure further provides a pharmaceutical composition that can be liquid or lyophilized (e.g., lyophilized from a liquid formulation) comprising adeno-associated virus (AAV) and about 10 mM L-histidine, about 20 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2.

The present disclosure further provides a pharmaceutical composition that can be liquid or lyophilized (e.g., lyophilized from a liquid formulation) comprising adeno-associated virus (AAV) and about 10 mM L-histidine, about 10 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2.

The present disclosure further provides a pharmaceutical composition that can be liquid or lyophilized (e.g., lyophilized from a liquid formulation) comprising adeno-associated virus (AAV) and about 10 mM L-histidine, about 0 mM sodium chloride, about 0.005% (w/v) polysorbate 80 (PS80), about 5% (w/v) trehalose, and about 50 mM glycine. In certain embodiments, the pH of the pharmaceutical composition is about 7.0±0.2.

Additional Components

In exemplary embodiments, the formulations or pharmaceutical compositions of the present disclosure comprise additional pharmaceutically acceptable ingredients. In exemplary aspects, the formulations or pharmaceutical compositions comprise any one or a combination of the following: acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. In some embodiments, the formulations or pharmaceutical compositions of the present disclosure comprise any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC)chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edentate, disodium edentate, disodium hydrogen phosphate, docusate calcium, docusate potassium, docusate sodium, dodecyl gallate, dodecyltrimethylammonium bromide, edentate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil type II, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, potassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), *theobroma* oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the Handbook of Pharmaceutical Excipients, Third Edition, A. H. Kibbe (Pharmaceutical Press, London, U K, 2000), which is incorporated by reference in its entirety. Remington's Pharmaceutical Sciences, Sixteenth Edition, E. W. Martin (Mack Publishing Co., Easton, Pa., 1980), which is incorporated by reference in its entirety for all intended purposes, discloses various components used in formulating pharmaceutically acceptable compositions and known techniques for the preparation thereof. Except insofar as any conventional agent is incompatible with the pharmaceutical compositions, its use in pharmaceutical compositions is contemplated. In exemplary embodiments, the formulations or pharmaceutical compositions of the present disclosure do not comprise one or a combination of the above ingredients. In exemplary embodiments, the formulations or pharmaceutical compositions of the present disclosure comprises none of these ingredients. In exemplary aspects, the pharmaceutical composition of the present disclosure does not comprise dextran. In exemplary aspects, the pharmaceutical composition of the present disclosure does not comprise calcium chloride.

pH

In exemplary embodiments, the pharmaceutical composition of the present disclosure has a physiologically compatible pH. Accordingly, in certain embodiments, the AAV formulations are provided that contain a buffering agent suitable to maintain the formulation at a neutral pH.

In exemplary aspects, the pH of the pharmaceutical composition is about 6.5 to about 9.0, about 6.5 to about 8.0, about 6.9 to about 7.7, or about 7.0 to about 7.5. In certain embodiments, the pH of the formulation is about 6.5 or about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In exemplary aspects, the pH of the pharmaceutical composition is about 7.0 or about 7.5. In certain embodiments, the pH of the pharmaceutical composition is about 7.0. In certain embodiments, the pH of the pharmaceutical composition is about 7.5.

Osmolality

In exemplary embodiments, the pharmaceutical composition of the present disclosure has an osmolality of about 200 to about 400 mOsmol/kg, about 250 to about 400 mOsmol/kg, or about 290 to about 390 mOsmol/kg. In certain embodiments, an AAV formulation provided herein will have an osmolality, for example, of about 200 mOsmol/L, about 210 mOsmol/L, about 220 mOsmol/L, about 230 mOsmol/L, about 240 mOsmol/L, about 250 mOsmol/L, about 260 mOsmol/L, about 270 mOsmol/L, about 280 mOsmol/L, about 290 mOsmol/L, about 300 mOsmol/L, about 310 mOsmol/L, about 320 mOsmol/L, about 330 mOsmol/L, about 340 mOsmol/L, about 350 mOsmol/L, about 360 mOsmol/L, about 370 mOsmol/L, about 380 mOsmol/L, about 390 mOsmol/L, or about 400 mOsmol/L. In exemplary aspects, the pharmaceutical composition of the present disclosure has an osmolality of about 250 mOsmol/kg to about 400 mOsmol/kg. In exemplary aspects, the pharmaceutical composition of the present disclosure has an osmolality of about 300±10 mOsmol/kg or about 380±10 mOsmol/kg. In certain embodiments, the pharmaceutical composition of the present disclosure has an osmolality of about 300±10 mOsmol/kg. In certain embodiments, the pharmaceutical composition of the present disclosure has an osmolality of about 380±10 mOsmol/kg.

Examples of tonicity agents that may be used in the formulations provided herein include, without limitation, sodium chloride, dextrose, sucrose, xylitol, fructose, glycerol, sorbitol, mannitol, trehalose, potassium chloride, mannose, calcium chloride, magnesium chloride, other inorganic salts, other sugars, other sugar alcohols, and combinations thereof. In certain embodiments, an AAV formulation may comprise at least one tonicity agent, or at least two, three, four, five, or more tonicity agents.

AAV

In exemplary embodiments, the pharmaceutical composition of the present disclosure comprises AAV. The AAV may be of any AAV serotype. In exemplary aspects, the AAV is of AAV1 serotype, AAV2 serotype, AAV3 serotype, AAV4 serotype, AAV5 serotype, AAV6 serotype, AAV7 serotype, AAV8 serotype, AAV9 serotype, or AAV10 serotype. In exemplary aspects, the AAV is of AAV8 serotype.

In certain embodiments of the formulations provided herein, the AAV is an rAAV as described in U.S. Patent Application Publication No. 2017/0233455 and provisional application No. 62/509,616, which are both incorporated herein by reference in their entirety and for all purposes.

In exemplary aspects, the pharmaceutical composition comprises a high titer AAV product. In exemplary aspects, the pharmaceutical composition comprises at least about $10^{10}$ virus particles (vp) or at least about $10^{11}$ virus particles (vp) or at least about $10^{12}$ virus particles (vp) or at least about $10^{13}$ virus particles (vp). In exemplary aspects, the pharmaceutical composition comprises at least about $10^{14}$ virus particles (vp) or at least about $10^{15}$ virus particles (vp), e.g., at least about $2\times10^{15}$ virus particles (vp), at least about $5\times10^{15}$ virus particles (vp). The pharmaceutical composition comprises also about $10^{10}$ vector genomes (vg) or at least about $10^{11}$ vector genomes (vg) or at least about $10^{12}$ vector genomes (vg) or at least about $10^{13}$ vector genomes (vg). In exemplary aspects, the pharmaceutical composition comprises at least about $10^{14}$ vector genomes (vg) or at least about $10^{15}$ vector genomes (vg), e.g., at least about $2\times10^{15}$ vector genomes (vg), at least about $5\times10^{15}$ vector genomes (vg).

Manufacture Methods and Uses

Methods of preparing a pharmaceutical composition comprising AAV are further provided herein. In exemplary aspects, the method comprises combining about 5 mM to about 25 mM buffering agent, about 50 mM to about 150 mM or less than about 100 mM pharmaceutically acceptable salt, about 0.001% (w/v) to about 0.01% (w/v) non-ionic surfactant, about 1% (w/v) to about 10% (w/v) sugar and/or sugar alcohol and AAV, thereby obtaining a pharmaceutical composition comprising AAV. In exemplary aspects, the method comprises preparing a composition, e.g., an aqueous solution, comprising about 5 mM to about 25 mM buffering agent, about 50 mM to about 150 mM or less than about 100 mM pharmaceutically acceptable salt, about 0.001% (w/v) to about 0.01% (w/v) non-ionic surfactant, about 1% (w/v) to about 10% (w/v) sugar and/or sugar alcohol and adding AAV to the composition. In exemplary aspects, the method comprises preparing a composition, e.g., an aqueous solution, comprising about 20 mM buffering agent, about 70 mM pharmaceutically acceptable salt, about 0.005% (w/v) non-ionic surfactant, and about 5% (w/v) sugar and/or sugar alcohol and adding AAV to the composition. In exemplary aspects, the method comprises preparing a composition, e.g., an aqueous solution, comprising about 10 mM buffering agent about 100 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 10 mM buffering agent about 80 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 10 mM buffering agent about 70 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 10 mM buffering agent about 60 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 10 mM buffering agent about 50 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 10 mM buffering agent about 40 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 10 mM buffering agent about 30 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 10 mM buffering agent about 20 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 10 mM buffering agent about 10 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 10 mM buffering agent about 0 mM pharmaceutically acceptable salt, about 0.005% (w/v) non-ionic surfactant, about 5% (w/v) sugar and/or sugar alcohol, and about 50 mM glycine and adding AAV to the composition. In exemplary aspects, the method comprises preparing a composition, e.g., an aqueous solution, comprising about 20 mM buffering agent, about 60 mM pharmaceutically acceptable salt, about 0.005% (w/v) non-ionic surfactant, about 35 mM sugar and/or sugar alcohol, and about 110 mM mannitol and adding AAV to the composition. In certain embodiments, the aqueous solution is lyophilized.

Methods of preparing a pharmaceutical composition comprising AAV are further provided herein. In exemplary aspects, the method comprises combining about 5 mM to about 25 mM L-histidine, about 50 mM to about 150 mM sodium chloride, about 0.001% (w/v) to about 0.01% (w/v) polysorbate 80 (PS80), about 1% (w/v) to about 10% (w/v) sucrose or trehalose and AAV, thereby obtaining a pharmaceutical composition comprising AAV. In exemplary aspects, the method comprises preparing a composition, e.g., an aqueous solution, comprising about 5 mM to about 25 mM L-histidine, about 50 mM to about 150 mM sodium chloride, about 0.001% (w/v) to about 0.01% (w/v) polysorbate 80 (PS80), and about 1% (w/v) to about 10% (w/v) sucrose or trehalose and adding AAV to the composition. In exemplary aspects, the method comprises preparing a composition, e.g., an aqueous solution, comprising about 20 mM L-histidine, about 70 mM sodium chloride, about 0.005% (w/v) polysorbate 80 (PS80), and about 5% (w/v) sucrose and adding AAV to the composition. In exemplary aspects, the method comprises preparing a composition, e.g., an aqueous solution, comprising about 10 mM L-histidine, about 100 mM sodium chloride, about 0.005% (w/v) polysorbate 80 (PS80), about 5% (w/v) trehalose, and about 50 mM glycine and adding AAV to the composition. In exemplary aspects, the method comprises preparing a composition, e.g., an aqueous solution, comprising about 10 mM L-histidine, about 80 mM sodium chloride, about 0.005% (w/v) polysorbate 80 (PS80), about 5% (w/v) trehalose, and about 50 mM glycine and adding AAV to the composition. In exemplary aspects, the method comprises preparing a composition, e.g., an aqueous solution, comprising about 10 mM L-histidine, about 70 mM sodium chloride, about 0.005% (w/v) polysorbate 80 (PS80), about 5% (w/v) trehalose, and about 50 mM glycine and adding AAV to the composition. In exemplary aspects, the method comprises preparing a composition, e.g., an aqueous solution, comprising about 10 mM L-histidine, about 60 mM sodium chloride, about 0.005% (w/v) polysorbate 80 (PS80), about 5% (w/v) trehalose, and about 50 mM glycine and adding AAV to the composition. In exemplary aspects, the method comprises preparing a composition, e.g., an aqueous solution, comprising about 10 mM L-histidine, about 50 mM sodium chloride, about 0.005% (w/v) polysorbate 80 (PS80), about 5% (w/v) trehalose, and about 50 mM glycine and adding AAV to the composition. In exemplary aspects, the method comprises preparing a composition, e.g., an aqueous solution, comprising about 10 mM L-histidine, about 40 mM sodium chloride, about 0.005% (w/v) polysorbate 80 (PS80), about 5% (w/v) trehalose, and about 50 mM glycine and adding AAV to the composition. In exemplary aspects, the method comprises preparing a composition, e.g., an aqueous solution, comprising about 10 mM L-histidine, about 30 mM sodium chloride, about 0.005% (w/v) polysorbate 80 (PS80), about 5% (w/v) trehalose, and about 50 mM glycine and adding AAV to the composition.

In exemplary aspects, the method comprises preparing a composition, e.g., an aqueous solution, comprising about 10 mM L-histidine, about 20 mM sodium chloride, about 0.005% (w/v) polysorbate 80 (PS80), about 5% (w/v) trehalose, and about 50 mM glycine and adding AAV to the composition. In exemplary aspects, the method comprises preparing a composition, e.g., an aqueous solution, comprising about 10 mM L-histidine, about 10 mM sodium chloride, about 0.005% (w/v) polysorbate 80 (PS80), about 5% (w/v) trehalose, and about 50 mM glycine and adding AAV to the composition. In exemplary aspects, the method comprises preparing a composition, e.g., an aqueous solution, comprising about 10 mM L-histidine, about 0 mM sodium chloride, about 0.005% (w/v) polysorbate 80 (PS80), about 5% (w/v) trehalose, and about 50 mM glycine and adding AAV to the composition. In exemplary aspects, the method comprises preparing a composition, e.g., an aqueous solution, comprising about 20 mM L-histidine, about 60 mM sodium chloride, about 0.005% (w/v) polysorbate 80 (PS80), about 35 mM trehalose, and about 110 mM mannitol and adding AAV to the composition. In certain embodiments, the aqueous solution is lyophilized.

In certain embodiments, lyophilization is used to produce a dehydrated composition, and thus the composition (e.g., the composition that contains the AAV) is a lyophilized composition. In some instances, a lyophilized composition is a composition where water has been removed from the composition by sublimation, where the water in the composition undergoes a phase transition from a solid to a gas. For example, a lyophilized composition may be a composition where water has been removed from the composition by freezing the composition (e.g., freezing the water in the composition) and then reducing the pressure surrounding the composition such that the water in the composition undergoes sublimation. As described above, a lyophilized composition may include water in a low amount, such as 25% or less, or 20% or less, or 15% or less, or 10% or less, or 9% or less, or 8% or less, or 7% or less, or 6% or less, or 5% or less, or 4% or less, or 3% or less, or 2% or less, or 1% or less, or 0.5% or less, or 0.25% or less, or 0.1% or less water as measured by Karl Fischer (KF) titration. In certain embodiments, a lyophilized composition has 3% or less water as measured by Karl Fischer titration. In certain embodiments, a lyophilized composition has 2% or less water as measured by Karl Fischer titration. In certain embodiments, a lyophilized composition has 1% or less water as measured by Karl Fischer titration. In certain embodiments, a lyophilized composition has 0.5% or less water as measured by Karl Fischer titration.

During lyophilization, the temperature of the composition may be reduced, for example to a temperature below the freezing point of water in the composition. For example, the temperature of the composition may be reduced to 0° C. or less, or –5° C. or less, or –10° C. or less, or –15° C. or less, or –20° C. or less, or –25° C. or less, or 30° C. or less, or –35° C. or less, or –40° C. or less, or –45° C. or less, or –50° C. or less, or 55° C. or less, or –60° C. or less, or –65° C. or less, or –75° C. or less. In some cases, the temperature of the composition is reduced to –20° C. In some cases, the temperature of the composition is reduced to –60° C. (set point –80° C.).

In certain embodiments, the pressure surrounding the composition is reduced below standard atmospheric pressure. For example, the pressure surrounding the composition may be reduced to 500 Torr or less, such as 250 Torr or less, or 100 Torr or less, or 50 Torr or less, or 10 Torr or less, or 1 Torr or less, or 500 mTorr or less, or 400 mTorr or less, or 300 mTorr or less, or 200 mTorr or less, or 100 mTorr or less, or 90 mTorr or less, or 80 mTorr or less, or 70 mTorr or less, or 60 mTorr or less, or 50 mTorr or less, or 40 mTorr or less, or 30 mTorr or less, or 20 mTorr or less, or 10 mTorr or less, or 5 mTorr or less, or 1 mTorr or less. In some cases, the pressure surrounding the composition is reduced to 40 to 50 mTorr or less, and such as 1.5 to 2 mTorr.

In some embodiments, lyophilizing may also include increasing the temperature of the composition while the pressure surrounding the composition is reduced. For example, the temperature of the composition may be increased from a minimum temperature as described above to a temperature greater than the minimum temperature. In some cases, the temperature is increased to facilitate sublimation of the water in the composition at the reduced surrounding pressure.

Embodiments of the method of making the lyophilized AAV composition may also include producing the aqueous concentrate composition, which is subsequently lyophilized.

In exemplary aspects, the method comprises placing the composition comprising AAV in a glass or plastic container, e.g., a glass vial, or a plastic tube. In exemplary aspects, the glass or plastic container is any one of those known in the art, commercially available, and/or described herein (see, e.g., Example 3). In exemplary aspects, the method comprises placing about 0.1 mL to about 10 ml of the composition comprising AAV into the glass or plastic container. In exemplary aspects, the method comprises placing about 0.2 mL to about 6 ml (e.g., about 0.2 ml, about 0.3 ml, about 0.5 mol, about 5.6 ml) of the composition comprising AAV into the glass or plastic container. Methods of preparing pharmaceutical compositions are described herein (see, e.g., Examples 1 and 2).

Providing the composition in a container may facilitate maintaining the composition as a sterile composition. For instance, the container may be configured to maintain the composition enclosed in the container in a sterile environment. As such, the container may be a sealed container, for example the container may include a seal, such as a water-tight and/or an air-tight seal. The seal may be removable from the container to allow a user access to the contents of the container. In some instances, the seal may be a frangible seal, or in other instances, the seal may be configured to allow insertion of a needle, cannula or syringe into the interior of the container without removing the seal from the container. In some cases, a seal configured to allow access to the interior of the container without removing the seal from the container may facilitate maintaining the contents of the container (e.g., the composition in the container) in a sterile environment prior to administration of the composition to a subject. Suitable materials for the seal include, for example, rubber or polymer seals, such as, but not limited to, silicone rubber, natural rubber, styrene butadiene rubber, ethylene-propylene copolymers, polychloroprene, polyacrylate, polybutadiene, polyurethane, styrene butadiene, and the like, and combinations thereof. For example, in certain embodiments, the seal is a septum pierceable by a needle, syringe, or cannula. The seal may also provide convenient access to a sample in the container, as well as a protective barrier that overlies the opening of the container. In some instances, the seal is a removable seal, such as a threaded or snap-on cap or other suitable sealing element that can be applied to the opening of the container. For instance, a threaded cap can be screwed over the opening before or after a sample has been added to the container.

In some cases, the container is a unit dosage container. A unit dosage container refers to a container that contains one or more unitary dosages for administration to a subject. In some embodiments, a unit dosage container includes a predetermined quantity of a subject composition calculated in an amount sufficient to produce a desired effect in a subject. Certain embodiments of the compositions may be provided in a unit dosage container suitable for individual administration of precise dosages. The amount of active composition administered to a subject may depend on the subject being treated, the severity of the affliction, and the manner of administration. For example, the unit dosage container may contain a quantity of the composition to be administered as disclosed herein in an amount effective to achieve the desired effect in the subject being treated. In certain instances, a unit dosage container includes a composition having a AAV in a therapeutically effective amount. In certain embodiments, the unit dosage container is a vial. In some cases, the vial is a sealed vial (e.g., as described above regarding a sealed container).

The container may be composed of any convenient material that is compatible with the AAV and other components of the composition. For example, the container can be a solid-compatible container configured to contain a solid (e.g., a lyophilized composition). In some instances, the container is a liquid-compatible container configured to contain a liquid. Containers may also be solid and liquid compatible, where the container is configured to contain solids and liquids. In some cases, a liquid in the container may be an aqueous liquid, and in these cases, the container may be compatible with aqueous compositions. By "compatible" is meant that the container is substantially inert (e.g., does not significantly react with) the liquid and/or compositions or other components in contact with the container. Examples of suitable container materials include, but are not limited to, glass and plastic. For example, the container may be composed of glass, such as, but not limited to, silicate glass, borosilicate glass, sodium borosilicate glass (e.g., PYREX™), fused quartz glass, fused silica glass, and the like. Other examples of suitable container materials for the container include plastics, such as, but not limited to, polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), polystyrene, and the like. In certain instances, as described above, the container is a vial, and as such may be a glass vial. As described above, the container may be a sealed container, and as such may be a sealed glass vial.

In exemplary aspects, the volume of the composition comprising AAV placed into the glass or plastic container is about 0.1 ml to about 10 ml, about 0.1 ml to about 5 ml, about 0.2 ml to about 6 ml, about 0.2 ml to about 5 ml, about 0.25 ml to about 5 ml, about 2 ml to about 5 ml, about 2.5 ml to about 5 ml, about 3 ml to about 5 ml, about 4 ml to about 5 ml, about 5 ml to about 10 ml, about 6 ml about 9 ml or about 7 ml to about 8 ml. In exemplary aspects, the volume about 0.1 ml about 0.2 ml, about 0.25 ml, about 0.3 ml, about 0.4 about 0.5 ml, about 0.6 ml, about 0.7 ml. about 0.75 ml, about 0.8 ml, about 0.9 ml, about 1 ml, about 2 ml, about 2.5 ml, about 3 ml, about 4 ml, about 5 ml, about 5.5 ml, about 5.6 ml, about 6 ml, about 7 ml, about 7.5 ml, about 8 ml, about 9 ml, or about 10 ml.

In exemplary aspects, the composition comprising AAV is stored at a temperature of about −80° C. to about −10° C. for at least 1 month (e.g., at least 2 months, at least 3 months, at least 4 months, at least 5 months, at least 6 months). In exemplary aspects, the composition comprising AAV is stored at a temperature of about −60° C. to about −20° C. for at least 1 month (e.g., at least 2 months, at least 3 months, at least 4 months, at least 5 months, at least 6 months). In exemplary aspects, the composition comprising AAV is stored for 3, 4, 5, or 6 months or longer. Methods of storing the composition are described herein (see, e.g., Examples 1 to 3). In exemplary aspects, greater than 80% of the initial amount of AAV (e.g., the amount of AAV in the composition prior to storage) is potent after the storage period (e.g., a storage period of about 3 months, about 4 months, about 5 months, or about 6 months or longer). In exemplary aspects, greater than 90% of the initial amount of AAV is potent after the storage period (e.g., a storage period of about 3 months, about 4 months, about 5 months, or about 6 months or longer). In exemplary aspects, greater than 95% of the initial amount of AAV is potent after the storage period (e.g., a storage period of about 3 months, about 4 months, about 5 months, or about 6 months or longer). In exemplary aspects, the biopotency of the AAV at the end of the storage period is substantially the same as the biopotency of the AAV at the beginning of the storage period. In exemplary aspects, the biopotency of the AAV at the end of the storage period is increased relative to the biopotency of the AAV at the beginning of the storage period. In exemplary aspects, the appearance of the composition at the end of the storage period is substantially the same as the composition at the beginning of the storage period. In exemplary aspects, the appearance of the composition at the end of the storage period is characterized by having no visible particles. In exemplary aspects, the particle concentration of the composition at the end of the storage period is substantially the same as the particle concentration of the composition at the beginning of the storage period. In exemplary aspects, the particle concentration of the composition at the end of the storage period is determined by microflow imaging (MFI).

Methods of treating a subject for a disorder treatable by gene therapy are provided by the present disclosure. In exemplary aspects, the method comprises administering to the subject a pharmaceutical composition as described herein in an amount effective to treat the disorder. In exemplary aspects, the disorder is a bleeding disorder (e.g., hemophilia A or B) and the method comprises administering to the subject a pharmaceutical composition of the present disclosure in an amount effective to treat the bleeding disorder.

In exemplary aspects, the methods comprise administering the pharmaceutical composition by parenteral administration. The term, "parenteral" means not through the alimentary canal but by some other route. For example, the formulations disclosed herein may be formulated for administration via known methods, such as intravenous administration (e.g., as a bolus or by continuous infusion over a period of time), by intramuscular, intraperitoneal, intracerobrospinal, subcutaneous, intra-articular, intrasynovial, intrathecal, oral, topical, or inhalation routes. In certain embodiments, the AAV formulations provided herein can be administered either systemically or locally. Systemic administration includes, without limitation: oral, subdermal, intraperitoneal, subcutaneous, transnasal, sublingual, or rectal routes of administration. Local administration includes, without limitation: topical, subcutaneous, intramuscular, and intraperitoneal routes of administration Methods of administering AAV for gene therapy of a subject are known in the art. See, e.g., Monahan, Gene therapy in an era of emerging treatment options for hemophilia B, J Thromb Haemost. 2015 June; 13(0 1): S151-S160.

Reconstituted compositions of the present disclosure may be administered to a subject, for example by injection or intravenously. In these embodiments, prior to administration of the reconstituted composition to a subject, a solid composition, e.g., as described above, may be combined with a liquid to provide a liquid composition suitable for administration, for example by injection or intravenously. In some cases, prior to administration of the composition to a subject, a solid composition may be combined with water (e.g., water for injection, WFI) or buffer/buffering agent (e.g., as described above) to provide an aqueous composition suitable for administration, for example by injection or intravenously. For instance, a lyophilized composition may be reconstituted with water (e.g., water for injection, WFI) or buffer/buffering agent (e.g., as described above) to produce a reconstituted dosage unit suitable for administration to a subject, for example by injection or intravenously.

In certain embodiments, the reconstituted dosage unit has a pH compatible with physiological conditions. In some cases, the pH of the reconstituted dosage unit ranges from 6 to 8. In some cases, the pH of the reconstituted dosage unit ranges from 7 to 8. For example, the pH of the reconstituted dosage unit may range from 7 to 7.5. In some cases, the pH of the reconstituted dosage unit is 7.0. In some cases, the pH of the reconstituted dosage unit is 7.1. In some cases, the pH of the reconstituted dosage unit is 7.2. In some cases, the pH of the reconstituted dosage unit is 7.3. In some cases, the pH of the reconstituted dosage unit is 7.4.

The reconstituted dosage unit may include a predetermined quantity of the composition of the present disclosure calculated in an amount sufficient to produce a desired therapeutic effect in a subject. The amount of the composition in a reconstituted dosage unit that is administered to a subject may depend on the subject being treated, the severity of the affliction, and the manner of administration. For example, the reconstituted dosage unit may include a quantity of the composition to be administered as disclosed herein in a therapeutically effective amount.

When administered to a subject, the liquid or reconstituted dosage unit may include a therapeutically effective amount of the AAV such that the reconstituted dosage unit delivers from 1E+10 vp/ml to 5E+15 vp/ml or 1E+10 cp/ml to 5E+15 cp/ml.

In certain embodiments, the method includes administering the liquid or reconstituted dosage unit to the subject according to a treatment regimen. For example, in some cases, a subject to be treated may have been prescribed a treatment regimen from a health care provider. In some cases, a treatment regimen includes, but is not necessarily limited to, administration five times per day, four times per day, three times per day, twice per day, once per day, three times per week, twice per week, once per week, once every two weeks, once every three weeks, once per month, once every 5 weeks, once every 6 weeks, once every 7 weeks, once every other month, and any combination thereof.

In some embodiments, the treatment regimen includes administering one or more doses over an extended period of time. In certain cases, a single dose (e.g., a single dosage unit) is administered to the subject, and the initial dose may be followed by one or more doses administered to the subject at a subsequent time. In some instances, more than one dose (e.g., more than one dosage unit) is administered to the subject, and the initial doses may be followed by one or more doses administered to the subject at a subsequent time. For example, a single dose (e.g., a single dosage unit) may be administered to the subject, and the single dose may be followed by a single dose administered to the subject at a subsequent time. Additional single doses may be administered at subsequent points in time. In other cases, a single dose (e.g., a single dosage unit) may be administered to the subject, and the single dose may be followed by two doses administered to the subject at a subsequent time. Additional single or multiple doses may be administered at subsequent points in time.

In certain embodiments, reconstituted dosage units of the present disclosure can be administered prior to, concurrent with, or subsequent to other active agents for treating related or unrelated conditions, e.g., in combination therapy. Examples of such additional therapies include radiation therapies, surgical therapies and chemotherapeutic therapies. If provided at the same time as other active agents, reconstituted dosage units of the present disclosure can be provided in the same or in a different formulation. For example, concurrent therapy may be achieved by administering a reconstituted dosage unit and a pharmaceutical composition having at least one other active agent, such as a chemotherapeutic agent, which in combination provide a therapeutically effective dose, according to a particular treatment regimen. Administration of separate pharmaceutical compositions can be performed simultaneously or at different times (e.g., sequentially, in either order, on the same day, or on different days), as long as a therapeutically effective effect of the combination of these substances is caused in the subject undergoing therapy.

Accordingly, aspects of the present disclosure further include combination therapies. In certain embodiments, the subject method includes administering a therapeutically effective amount of one or more additional active agents. By combination therapy is meant that a AAV composition (e.g., as described herein) can be used in a combination with another therapeutic agent to treat a single disease or condition. In certain embodiments, a compound of the present disclosure is administered concurrently with the administration of another therapeutic agent, which can be administered as a component of a composition including the compound of the present disclosure or as a component of a different composition. In certain embodiments, a composition including a compound of the present disclosure is administered prior or subsequent to administration of another therapeutic agent.

The following examples are given merely to illustrate the present invention and not in any way to limit its scope.

EXAMPLES

Example 1

This example demonstrates initial studies that led to the selection of three formulations for further development.

Six different formulations were manufactured. Briefly, a single lot comprising mostly empty capsid material was diluted with PBS/NaCl/Sorbitol buffer to generate 180.8 g. The solution was spiked with 0.005% Croda super refined Tween 80 to prevent excessive material loss via adsorption. This solution was divided into 6 parts, each containing 30 g material. The buffer solution was then changed into one of the six buffers using Slide-A-Lyzer dialysis cassettes and this step was performed three times with 100-fold volume. After the three dialysis steps, each of the dialyzed solutions were filled into 2-ml $SiO_2$ vials (filling volume=0.25 ml) and then stored at −20±2° C. and ≤−60° C. (set point: −80° C.) for up to 6 months and at 5±3° C. for up to 4 months. Tables 1-6 describe Formulations 1-6 (also referred to as Buffers 1-6, and Samples 1-6), respectively.

TABLE 1

Formulation 1: PBS/NaCl/Sorbitol buffer with Polysorbate 80 (PS80)

| Excipient | Concentration [mM] | Concentration g/kg buffer |
|---|---|---|
| Sodium chloride | 350 | 20.45 |
| Potassium chloride | 2.68 | 0.20 |
| Disodiumhydrogenphosphate-Dihydrate | 8.09 | 1.44 |
| Monopotassium phosphate | 1.47 | 0.20 |
| D-Sorbitol | 5% | 50.00 |
| Croda super refined Tween 80 (PS80) | 0.005% | 0.05 |
| 25% HCl | | pH adjustment |
| 1M NaOH | | |
| Purified water | | add to 1 kg |
| pH value | 7.4 ± 0.3 | |

TABLE 2

Formulation 2

| Excipient | Concentration [mM] | Concentration g/kg buffer |
|---|---|---|
| L-histidine | 20 | 3.103 |
| NaCl | 70 | 4.091 |
| Sucrose | 5% | 50.00 |
| Croda super refined Tween 80 (PS80) | 0.005% | 0.050 |
| Purified water | | add to 1 kg |
| pH value | 7.5 | |

TABLE 3

Formulation 3

| Excipient | Concentration [mM] | Concentration g/kg buffer |
|---|---|---|
| L-histidine | 20 | 3.103 |
| NaCl | 60 | 3.506 |
| Mannitol | 110 | 20.039 |
| Trehalose Dihydrate | 35 | 13.24 |
| Croda super refined Tween 80 (PS80) | 0.005% | 0.05 |
| Purified water | | add to 1 kg |
| pH value | 7.0 ± 0.1 | |

TABLE 4

Formulation 4

| Excipient | Concentration [mM] | Concentration g/kg buffer |
|---|---|---|
| L-histidine | 10 | 1.552 |
| NaCl | 100 | 5.844 |
| Glycine | 50 | 3.754 |
| Trehalose Dihydrate | 5% | 50.00 |
| Croda super refined Tween 80 | 0.005% | 0.05 |
| Purified water | | add to 1 kg |
| pH value | 7.0 ± 0.1 | |

TABLE 5

Formulation 5

| Excipient | Concentration [mM] | Concentration g/kg buffer |
|---|---|---|
| Tri-Sodium Citrate-di-Hydrate | 15 | 4.41 |
| Glycine | 15 | 1.11 |

TABLE 5-continued

Formulation 5

| Excipient | Concentration [mM] | Concentration g/kg buffer |
|---|---|---|
| Mannitol | 2% | 20.00 |
| Trehalose Dihydrate | 1% | 10.00 |
| Croda super refilled Tween 80 (PS80) | 0.005% | 0.05 |
| Purified water | | add to 1 kg |
| pH value | | 7.3 ± 0.1 |

TABLE 6

Formulation 6

| Excipient | Concentration [mM] | Concentration g/kg buffer |
|---|---|---|
| TRIS | 80 | 9.691 |
| Dextran T40 | 1.77% | 17.70 |
| Dextran T10 | 0.53% | 5.30 |
| Sucrose | 6.9% | 69.00 |
| Croda super refined Tween 80 (PS80) | 0.005% | 0.05 |
| Purified water | | add to 1 kg |
| pH value | | 7.1 |

The total particle titer (empty+full) was tested by a total rAAV particle ELISA. AAV purity and chemical degradation was tested by SDS-PAGE (fluorescence staining, 4-12% BisTris gel with Flamingo Stain). Physical degradation (damaged capsids or fragments) were tested by SEC and MFI. The appearance and pH were also tested.

The formulations stored at −20±2° C. and −60° C. (set point: −80° C.) were tested for MFI, appearance, pH, total rAAV8 particle ELISA, SDS-PAGE, and SEC at the test time points indicated in Table 7. An "-" indicates no samples were taken.

TABLE 7

Study outline for samples stored at −20 ± 2° C. and ≤−60° C. (*set point −80° C.)

| | | Test Time Point (months) | | | | | TOTAL Number of Samples |
|---|---|---|---|---|---|---|---|
| Test | Sample Volume | 0 | 1 | 2 8 weeks | 3 | 6 | |
| MFI | 3 ml | x | — | — | — | x | 50 |
| Appearance | 1 ml | x | x | x | x | x | 10 |
| pH value | | x | x | x | x | x | |
| Total rAAV8 particle ELISA | 2× 0.3 ml | x | x | x | x | x | 100 |
| SDS-PAGE (fluorescence staining, 4-12% BisTris gel with Flamingo Stain) | 0.3 ml | x | x | x | x | x | 50 |
| SEC | 0.3 ml | x | x | x | x | x | 50 |

The formulations stored at 5±3° C. were tested for MFI, appearance, pH, total rAAV8 particle ELISA, SDS-PAGE, and SEC at the test time points indicated in Table 8. An "-" indicates no samples were taken.

TABLE 8

Study outline for samples stored at +5 ± 3° C.

| | | Test time point (months) | | | | Total Number of Samples |
|---|---|---|---|---|---|---|
| Test | Sample Volume | 0 | 1 | 2 (8 weeks) | 4 | |
| MFI | 3 ml | x | — | — | — | x |
| Appearance | 1 ml | x | x | x | x | 20 |
| pH value | | x | x | x | x | |
| Total rAAV8 particle ELISA | 2x 0.3 ml | x | x | x | x | 40 |
| SDS-PAGE (fluorescence staining, 4-12% BisTris gel with Flamingo Stain) | 0.3 ml | x | x | x | x | 20 |
| SEC | 0.3 ml | x | x | x | x | 20 |

Results of the appearance test are shown in Table 9, wherein the classification of particles inspection with an unaided eye were as follows: Level A=no particles visible; Level B=small single particles, barely visible; Level C=small single particles, easily visible; Level D many small particles, easily visible; and Level E=particles visible greater than or equal to 1 mm.

TABLE 9

Appearance with storage at +5 ± 3° C., −20 ± 2° C., and ≤−60° C.

| testing time point/buffer at +5 ± 3° C. | 0 months | 1 month | 8 weeks | 4 months |
|---|---|---|---|---|
| buffer 1 at +5 ± 3° C. | A | A-B | A-B | C |
| buffer 2 at +5 ± 3° C. | A | A | A | A |
| buffer 3 at +5 ± 3° C. | A | A | A | A |
| buffer 4 at +5 ± 3° C. | A | A | A | A |
| buffer 5 at +5 ± 3° C. | A | A | A | A |
| buffer 6 at +5 ± 3° C. | A (yellow) | A (yellow) | A (yellow) | A (yellow) |

| testing time point/buffer at −20 ± 2° C. | 0 months | 1 month | 8 weeks | 3 months | 6 months |
|---|---|---|---|---|---|
| buffer 1 at −20 ± 2° C. | A | A-B | A-B | A-B | A-B |
| buffer 2 at −20 ± 2° C. | A | A | A | A | A |
| buffer 3 at −20 ± 2° C. | A | A | A | A | A |
| buffer 4 at −20 ± 2° C. | A | A | A | A | A |

TABLE 9-continued

Appearance with storage at +5 ± 3° C., −20 ± 2° C., and ≤−60° C.

| | | | | | |
|---|---|---|---|---|---|
| buffer 5 at −20 ± 2° C. | A | A | A | A | A |
| buffer 6 at −20 ± 2° C. | A (yellow) | A (yellow) | A (yellow) | A (yellow) | A (yellow) |
| testing time point/buffer at ≤−60° C. | | | | | |
| buffer 1 at ≤−60° C. | A | A-B | A-B | A | A |
| buffer 2 at ≤−60° C. | A | A | A | A | A |
| buffer 3 at ≤−60° C. | A | A | A | A | A |
| buffer 4 at ≤−60° C. | A | A | A | A | A |
| buffer 5 at ≤−60° C. | A | A | A | A | A |
| buffer 6 at ≤−60° C. | A (yellow) | A (yellow) | A (yellow) | A (yellow) | A (yellow) |

Results of the pH assays are shown in Table 10. No significant shifts can be seen for the pH values after being stored at 5±3° C. for up to 4 months and at −20±2° C. and −60° C. for up to 6 months after thawing them.

TABLE 10

Total pH values with storage at +5 ± 3° C., −20 ± 2° C., and ≤−60° C.

| testing time point/buffer at +5 ± 3° C. | target pH value | 0 months | 1 month | 8 weeks | 4 months |
|---|---|---|---|---|---|
| buffer 1 at +5 ± 3° C. | 7.4 | 7.24 | 7.29 | 7.31 | 7.31 |
| buffer 2 at +5 ± 3° C. | 7.5 | 7.37 | 7.38 | 7.40 | 7.47 |
| buffer 3 at +5 ± 3° C. | 7.0 | 6.86 | 6.95 | 7.00 | 7.01 |
| buffer 4 at +5 ± 3° C. | 7.0 | 6.93 | 6.89 | 7.01 | 7.01 |
| buffer 5 at +5 ± 3° C. | 7.3 | 7.22 | 7.08 | 7.13 | 7.23 |
| buffer 6 at +5 ± 3° C. | 7.1 | 7.12 | 7.11 | 7.10 | 7.09 |

| testing time point/buffer at −20 ± 2° C. | target pH value | 0 months | 1 month | 8 weeks | 3 months | 6 months |
|---|---|---|---|---|---|---|
| buffet 1 at −20 ± 2° C. | 7.4 | 7.24 | 7.32 | 7.33 | 7.34 | 7.33 |
| buffer 2 at −20 ± 2° C. | 7.5 | 7.37 | 7.37 | 7.42 | 7.40 | 7.38 |
| buffer 3 at −20 ± 2° C. | 7.0 | 6.86 | 7.00 | 7.02 | 7.00 | 7.00 |
| buffer 4 at −20 ± 2° C. | 7.0 | 6.93 | 6.97 | 6.99 | 6.97 | 6.99 |
| buffer 5 at −20 ± 2° C. | 7.3 | 7.22 | 6.90 | 6.93 | 6.92 | 6.93 |
| buffer 6 at −20 ± 2° C. | 7.1 | 7.12 | 6.88 | 6.98 | 6.98 | 6.98 |

| testing time point/buffer at ≤−60° C. | target pH value | 0 months | 1 month | 8 weeks | 3 months | 6 months |
|---|---|---|---|---|---|---|
| buffer 1 at ≤−60° C. | 7.4 | 7.24 | 7.31 | 7.34 | 7.34 | 7.31 |
| buffer 2 at ≤−60° C. | 7.5 | 7.37 | 7.40 | 7.42 | 7.41 | 7.39 |
| buffer 3 at ≤−60° C. | 7.0 | 6.86 | 6.98 | 7.04 | 7.01 | 7.00 |
| buffer 4 at ≤−60° C. | 7.0 | 6.93 | 6.89 | 7.00 | 7.00 | 7.00 |
| buffer 5 at ≤−60° C. | 7.3 | 7.22 | 6.88 | 6.93 | 6.94 | 6.92 |
| buffer 6 at ≤−60° C. | 7.1 | 7.12 | 6.86 | 6.98 | 6.98 | 6.97 |

Results of the AAV8 titration ELISA are shown in Table 11. All results during storage at 5±3° C., −20±2° C., and −60° C. do not show any significant differences among the six formulations investigated. Harmonized results (calculated with 0.44) are shown.

TABLE 11

Calculated AAV8 Titration ELISA with storage at +5 ± 3° C., −20 ± 2° C., and ≤−60° C.

| testing time point/buffer at +5 ± 3° C. | 0 months | 1 month | 8 weeks | 4 months |
|---|---|---|---|---|
| buffer 1 at +5 ± 3° C. | 1.45E+13 | 1.74E+13 | 2.43E+13 | 1.77E+13 |
| buffer 2 at +5 ± 3° C. | 1.45E+13 | 1.57E+13 | 1.93E+13 | 1.80E+13 |
| buffer 3 at +5 ± 3° C. | 1.31E+13 | 1.49E+13 | 1.94E+13 | 1.64E+13 |
| buffer 4 at +5 ± 3° C. | 1.46E+13 | 1.57E+13 | 2.00E+13 | 1.92E+13 |

TABLE 11-continued

Calculated AAV8 Titration ELISA with storage at +5 ± 3° C., −20 ± 2° C., and ≤−60° C.

| | | | | |
|---|---|---|---|---|
| buffer 5 at +5 ± 3° C. | 1.41E+13 | 1.52E+13 | 2.02E+13 | 1.72E+13 |
| buffer 6 at +5 ± 3° C. | 1.74E+13 | 1.88E+13 | 2.42E+13 | 2.09E+13 |

| | 0 months | 1 month | 8 weeks | 3 months | 6 months |
|---|---|---|---|---|---|
| testing time point/buffer at −20 ± 2° C. | | | | | |
| buffer 1 at −20 ± 2° C. | 1.45E+13 | 1.58E+13 | 1.93E+13 | 1.89E+13 | 1.92E+13 |
| buffer 2 at −20 ± 2° C. | 1.45E+13 | 1.59E+13 | 1.83E+13 | 1.87E+13 | 1.89E+13 |
| buffer 3 at −20 ± 2° C. | 1.31E+13 | 1.48E+13 | 1.70E+13 | 1.74E+13 | 1.71E+13 |
| buffer 4 at −20 ± 2° C. | 1.46E+13 | 1.57E+13 | 1.82E+13 | 1.86E+13 | 1.95E+13 |
| buffer 5 at −20 ± 2° C. | 1.41E+13 | 1.47E+13 | 1.78E+13 | 1.78E+13 | 1.81E+13 |
| buffer 6 at −20 ± 2° C. | 1.74E+13 | 1.89E+13 | 2.22E+13 | 2.29E+13 | 2.19E+13 |
| testing time point/buffer at ≤−60° C. | | | | | |
| buffer 1 at ≤−60° C. | 1.45E+13 | 1.58E+13 | 2.03E+13 | 1.80E+13 | 1.72E+13 |
| buffer 2 at ≤−60° C. | 1.45E+13 | 1.57E+13 | 2.19E+13 | 1.86E+13 | 1.72E+13 |
| buffer 3 at ≤−60° C. | 1.31E+13 | 1.50E+13 | 1.76E+13 | 1.76E+13 | 1.73E+13 |
| buffer 4 at ≤−60° C. | 1.46E+13 | 1.65E+13 | 1.94E+13 | 1.78E+13 | 1.43E+13 |
| buffer 5 at ≤−60° C. | 1.41E+13 | 1.51E+13 | 1.82E+13 | 1.80E+13 | 1.64E+13 |
| buffer 6 at ≤−60° C. | 1.74E+13 | 1.98E+13 | 2.44E+13 | 2.13E+13 | 1.54E+13 |

Percent aggregates were measured as shown in Table 12. Higher aggregate values were seed for Formulation 3 at 0 months and after storage at 5±3° C. and at −60° C. All other buffers show fluctuating values.

TABLE 12

Aggregates [%] with storage at +5 ± 3° C., −20 ± 2° C., and ≤−60° C.

| testing time point/buffer at +5 ± 3° C. | 0 months | 1 month | 8 weeks | 4 months |
|---|---|---|---|---|
| buffer 1 at +5 ± 3° C. | 1.55 | 1.50 | 1.90 | 1.84 |
| buffer 2 at +5 ± 3° C. | 1.59 | 1.50 | 1.57 | 1.85 |
| buffer 3 at +5 ± 3° C. | 2.34 | 1.75 | 2.00 | 1.93 |
| buffer 4 at +5 ± 3° C. | 1.56 | 1.57 | 1.50 | 1.69 |
| buffer 5 at +5 ± 3° C. | 1.72 | 1.81 | 1.49 | 1.81 |
| buffer 6 at +5 ± 3° C. | 1.64 | 1.76 | 1.88 | 1.85 |

| | 0 months | 1 month | 8 weeks | 3 months | 6 months |
|---|---|---|---|---|---|
| testing time point/buffer at −20 ± 2° C. | | | | | |
| buffer 1 at −20 ± 2° C. | 1.55 | 1.47 | 2.21 | 1.31 | 1.41 |
| buffer 2 at −20 ± 2° C. | 1.59 | 1.52 | 2.24 | 1.43 | 1.42 |

TABLE 12-continued

Aggregates [%] with storage at +5 ± 3° C., −20 ± 2° C., and ≤−60° C.

| | | | | | |
|---|---|---|---|---|---|
| buffer 3 at −20 ± 2° C. | 2.34 | 1.49 | 1.74 | 1.37 | 1.44 |
| buffer 4 at −20 ± 2° C. | 1.56 | 1.58 | 1.53 | 1.38 | 1.50 |
| buffer 5 at −20 ± 2° C. | 1.72 | 1.70 | 1.43 | 1.90 | 1.54 |
| buffer 6 at −20 ± 2° C. | 1.64 | 1.69 | 2.78 | 2.41 | 1.87 |
| testing time point/buffer at ≤−60° C. | | | | | |
| buffer 1 at ≤−60° C. | 1.55 | 1.54 | 2.30 | 1.38 | 1.47 |
| buffer 2 at ≤−60° C. | 1.59 | 1.53 | 1.70 | 1.46 | 1.51 |
| buffer 3 at ≤−60° C. | 2.34 | 2.25 | 1.95 | 1.61 | 2.27 |
| buffer 4 at ≤−60° C. | 1.56 | 1.52 | 1.63 | 1.49 | 1.46 |
| buffer 5 at ≤−60° C. | 1.72 | 2.81 | 2.07 | 2.26 | 1.95 |
| buffer 6 at ≤−60° C. | 1.64 | 1.58 | 1.93 | 1.47 | 1.59 |

The results of the SDS-PAGE assays are shown in Tables 13-18, showing measurements at 0, 1, 2, 3, 4, and 6 months. All samples show stability during storage time for all temperatures except Buffer 1, that shows an additional band at 163 kDa after 4 months' storage at 5±3° C.

TABLE 13

Purity and summary with storage time = 0 months

| Band | Sample 1 Band % | Sample 2 Band % | Sample 3 Band % | Sample 4 Band % | Sample 5 Band % | Sample 6 Band % |
|---|---|---|---|---|---|---|
| VP1 | 15.85 | 15.33 | 16.11 | 16.58 | 16.62 | 16.43 |
| VP2 | 22.55 | 22.92 | 22.08 | 23.58 | 23.4 | 24.51 |
| VP3 | 61.6 | 61.75 | 61.82 | 59.84 | 59.98 | 59.06 |
| SUM VP1 + VP2 + VP3 | 100.0 | 100.0 | 100.0 | 100.0 | 100.0 | 100.0 |

TABLE 14

Purity and summary with storage time = 1 month at +5 ± 3° C.

| Band | Sample 1 lane 3 Band % | Sample 2 lane 4 Band % | Sample 3 lane 5 Band % | Sample 4 lane 6 Band % | Sample 5 lane 7 Band % | Sample 6 lane 8 Band % |
|---|---|---|---|---|---|---|
| VP1 | 15.8 | 16.7 | 16.5 | 16.6 | 16.6 | 17.3 |
| VP2 | 27.1 | 27.1 | 26.3 | 26.7 | 26.2 | 26.7 |
| VP3 | 57.2 | 56.2 | 57.3 | 56.6 | 57.2 | 56.0 |
| SUM VP1 + VP2 + VP3 | 100.0 | 100.0 | 100.0 | 100.0 | 100.0 | 100.0 |

Purity and summary with storage time = 1 month at −20 ± 2° C.

| Band | Sample 1 lane 9 Band % | Sample 2 lane 10 Band % | Sample 3 lane 11 Band % | Sample 4 lane 12 Band % | Sample 5 lane 13 Band % | Sample 6 lane 14 Band % |
|---|---|---|---|---|---|---|
| VP1 | 16.8 | 16.7 | 16.3 | 17.1 | 16.6 | 17.0 |
| VP2 | 26.1 | 26.2 | 26.2 | 26.2 | 25.4 | 26.3 |
| VP3 | 57.2 | 57.1 | 57.5 | 56.8 | 58.1 | 56.7 |
| SUM VP1 + VP2 + VP3 | 100.0 | 100.0 | 100.0 | 100.0 | 100.0 | 100.0 |

Purity and summary with storage time = 1 month at ≤−60° C.

| Band | Sample 1 lane 15 Band % | Sample 2 lane 16 Band % | Sample 3 lane 17 Band % | Sample 4 lane 18 Band % | Sample 5 lane 19 Band % | Sample 6 lane 20 Band % |
|---|---|---|---|---|---|---|
| VP1 | 16.5 | 16.5 | 16.3 | 16.4 | 16.4 | 17.7 |
| VP2 | 26.3 | 26.8 | 26.1 | 26.9 | 26.5 | 27.2 |
| VP3 | 57.2 | 56.7 | 57.6 | 56.7 | 57.1 | 55.1 |
| SUM VP1 + VP2 + VP3 | 100.0 | 100.0 | 100.0 | 100.0 | 100.0 | 100.0 |

TABLE 15

Purity and summary with storage time = 2 months at +5 ± 3° C.

| Band | Sample 1 Lane 3 Band % | Sample 2 Lane 4 Band % | Sample 3 Lane 5 Band % | Sample 4 Lane 6 Band % | Sample 5 Lane 7 Band % | Sample 6 Lane 8 Band % |
|---|---|---|---|---|---|---|
| VP1 | 15.3 | 16.2 | 16.3 | 16.3 | 16.6 | 16.9 |
| VP2 | 26.6 | 26.5 | 26.4 | 26.4 | 26.5 | 26.4 |
| VP3 | 58.1 | 57.3 | 57.3 | 57.4 | 56.9 | 56.7 |
| SUM VP1 + VP2 + VP3 | 100.0 | 100.0 | 100.0 | 100.0 | 100.0 | 100.0 |

Purity and summary with storage time = 2 months at −20 ± 2° C.

| Band | Sample 1 Lane 9 Band % | Sample 2 Lane 10 Band % | Sample 3 Lane 11 Band % | Sample 4 Lane 12 Band % | Sample 5 Lane 13 Band % | Sample 6 Lane 14 Band % |
|---|---|---|---|---|---|---|
| VP1 | 16.1 | 16.5 | 16.1 | 16.2 | 16.2 | 16.8 |
| VP2 | 26.6 | 27.2 | 26.5 | 26.7 | 26.1 | 26.6 |
| VP3 | 57.4 | 56.3 | 57.4 | 57.1 | 57.7 | 56.6 |
| SUM VP1 + VP2 + VP3 | 100.0 | 100.0 | 100.0 | 100.0 | 100.0 | 100.0 |

Purity and summary with storage time = 2 months at ≤−60° C.

| Band | Sample 1 Lane 15 Band % | Sample 2 Lane 16 Band % | Sample 3 Lane 17 Band % | Sample 4 Lane 18 Band % | Sample 5 Lane 19 Band % | Sample 6 Lane 20 Band % |
|---|---|---|---|---|---|---|
| VP1 | 16.4 | 16.5 | 16.4 | 16.7 | 16.9 | 17.7 |
| VP2 | 26.5 | 26.8 | 26.4 | 26.5 | 26.7 | 27.3 |
| VP3 | 57.1 | 56.6 | 57.2 | 56.7 | 56.5 | 55.0 |
| SUM VP1 + VP2 + VP3 | 100.0 | 100.0 | 100.0 | 100.0 | 100.0 | 100.0 |

TABLE 16

Purity and summary with storage time = 3 months at −20 ± 2° C.

| Band | Sample 1 Lane 5 Band % | Sample 2 Lane 6 Band % | Sample 3 Lane 7 Band % | Sample 4 Lane 8 Band % | Sample 5 Lane 9 Band % | Sample 6 Lane 10 Band % |
|---|---|---|---|---|---|---|
| VP1 | 19.58 | 18.95 | 18.78 | 18.6 | 18.69 | 18.45 |
| VP2 | 27.6 | 27.33 | 27.65 | 27.32 | 27.31 | 27.21 |
| VP3 | 52.82 | 53.72 | 53.57 | 54.08 | 53.99 | 54.35 |
| SUM VP1 + VP2 + VP3 | 100 | 100 | 100 | 100 | 100 | 100 |

Purity and summary with storage time = 3 months at ≤−60° C.

| Band | Sample 1 Lane 12 Band % | Sample 2 Lane 13 Band % | Sample 3 Lane 14 Band % | Sample 4 Lane 15 Band % | Sample 5 Lane 16 Band % | Sample 6 Lane 17 Band % |
|---|---|---|---|---|---|---|
| VP1 | 18.6 | 18.49 | 18.91 | 19.14 | 19.08 | 19.07 |
| VP2 | 27.06 | 26.6 | 27.69 | 27.04 | 27.81 | 27.57 |
| VP3 | 54.34 | 54.92 | 53.4 | 53.82 | 53.12 | 53.36 |
| SUM VP1 + VP2 + VP3 | 100 | 100 | 100 | 100 | 100 | 100 |

TABLE 17

Purity and summary with storage time = 4 months at +5 ± 3° C.

| Band | Sample 1 Lane 5 Band % | Sample 2 Lane 6 Band % | Sample 3 Lane 7 Band % | Sample 4 Lane 8 Band % | Sample 5 Lane 9 Band % | Sample 6 Lane 10 Band % |
|---|---|---|---|---|---|---|
|  | 5.39 |  |  |  |  |  |
| VP1 | 15.75 | 17.96 | 18.03 | 18.42 | 17.99 | 17.66 |
| VP2 | 27.73 | 27.83 | 28.56 | 28.27 | 29.06 | 28.2 |
| VP3 | 51.12 | 54.21 | 53.42 | 53.31 | 52.94 | 54.14 |
| SUM VP1 + VP2 + VP3 | 94.6 | 100 | 100 | 100 | 100 | 100 |

TABLE 18

Purity and summary with storage time = 6 months at −20 ± 2° C.

| Band | Sample 1 lane 5 Band % | Sample 2 lane 6 Band % | Sample 3 lane 7 Band % | Sample 4 lane 8 Band % | Sample 5 lane 9 Band % | Sample 6 lane 10 Band % |
|---|---|---|---|---|---|---|
| VP1 | 19.26 | 19.27 | 19.01 | 18.81 | 18.59 | 18.72 |
| VP2 | 27.79 | 27.64 | 26.85 | 27.25 | 26.93 | 26.83 |
| VP3 | 52.95 | 53.09 | 54.14 | 53.94 | 54.48 | 54.45 |
| SUM VP1 + VP2 + VP3 | 100.0 | 100.0 | 100.0 | 100.0 | 100.0 | 100.0 |

Purity and summary with storage time = 6 months at ≤−60° C.

| Band | Sample 1 lane 12 Band % | Sample 2 lane 13 Band % | Sample 3 lane 14 Band % | Sample 4 lane 15 Band % | Sample 5 lane 16 Band % | Sample 6 lane 17 Band % |
|---|---|---|---|---|---|---|
| VP1 | 18.63 | 18.33 | 18.46 | 18.73 | 18.8 | 18.94 |
| VP2 | 26.83 | 26.61 | 27.29 | 26.5 | 26.53 | 27.16 |
| VP3 | 54.54 | 55.07 | 54.25 | 54.77 | 54.67 | 53.9 |
| SUM VP1 + VP2 + VP3 | 100.0 | 100.0 | 100.0 | 100.0 | 100.0 | 100.0 |

The results of the subvisible particle concentration of material using MFI are shown in Tables 19-23. This assay was performed to observe subvisible particle generation during storage of AAV material at 5±3° C. for 4 months and at −20±2° C. and ° C. for 6 months.

TABLE 19

Comparison of particles ≥10 μm (number/ml)

| sample | 0 months | 4 months +5 ± 3° C. | 6 months −20 ± 2° C. | 6 months ≤−60° C. |
|---|---|---|---|---|
| Sample 1 | 515.89 | | 478.03 | 606.05 |
| Sample 2 | 548.45 | 826.43 | 748.80 | 688.69 |
| Sample 3 | 550.95 | 1179.54 | 1570.22 | 1450.01 |
| Sample 4 | 578.50 | 593.53 | | 668.66 |
| Sample 5 | 813.91 | 5086.30 | 4299.94 | 4675.59 |
| Sample 6 | 1014.25 | 437.65 | | |

TABLE 20

Comparison of particles ≥25 μm (number/ml)

| sample | 0 months | 4 months +5 ± 3° C. | 6 months −20 ± 2° C. | 6 months ≤−60° C. |
|---|---|---|---|---|
| Sample 1 | 100.17 | | 117.63 | 157.77 |
| Sample 2 | 95.16 | 127.72 | 175.30 | 152.76 |
| Sample 3 | 107.69 | 363.13 | 250.43 | 185.32 |
| Sample 4 | 120.21 | 107.69 | | 152.76 |
| Sample 5 | 127.72 | 833.94 | 558.47 | 548.45 |
| Sample 6 | 272.97 | 83.00 | | |

TABLE 21

Particle concentration at 0 months

| Measurement | ≥1 μm | ≥2 μm | ≥5 μm | ≥10 μm | ≥25 μm | ≥50 μm | ≥70 μm |
|---|---|---|---|---|---|---|---|
| Sample 1 | 29107.85 | 9408.77 | 1803.12 | 515.89 | 100.17 | 20.03 | 7.51 |
| Sample 2 | 34912.89 | 10653.43 | 1878.25 | 548.45 | 95.16 | 12.52 | 2.50 |
| Sample 3 | 35030.59 | 10250.23 | 1783.08 | 550.95 | 107.69 | 25.04 | 10.02 |
| Sample 4 | 30908.46 | 9303.59 | 1798.11 | 578.50 | 120.21 | 17.53 | 5.01 |
| Sample 5 | 48681.70 | 12366.39 | 2376.61 | 813.91 | 127.72 | 20.03 | 2.50 |
| Sample 6 | 39713.69 | 11710.25 | 2784.82 | 1014.25 | 272.97 | 67.62 | 35.06 |

TABLE 22

Particle concentration after 4 months at +5 ± 3° C.

| Measurement | ≥1 μm | ≥2 μm | ≥5 μm | ≥10 μm | ≥25 μm | ≥50 μm | ≥70 μm |
|---|---|---|---|---|---|---|---|
| Sample 2 +5 ± 3° C. | 22999.78 | 11469.84 | 3551.14 | 826.43 | 127.72 | 22.54 | 2.50 |
| Sample 3 +5 ± 3° C. | 11504.90 | 5088.80 | 2033.52 | 1179.54 | 363.13 | 72.63 | 40.07 |
| Sample 4 +5 ± 3° C. | 28096.10 | 9498.93 | 1808.13 | 593.53 | 107.69 | 27.55 | 10.02 |
| Sample 5 +5 ± 3° C. | 19516.26 | 11943.16 | 7798.49 | 5086.30 | 833.94 | 75.13 | 22.54 |
| Sample 6 +5 ± 3° C. | 20710.38 | 6235.25 | 1466.38 | 437.65 | 83.00 | 22.64 | 7.55 |

TABLE 23

Particle concentration after 6 months at −20 ± 2° C. and ≤−60° C.

| Measurement | ≥1 μm | ≥2 μm | ≥5 μm | ≥10 μm | ≥25 μm | ≥50 μm | ≥70 μm |
|---|---|---|---|---|---|---|---|
| Sample 1 −20° C. | 24131.83 | 6790.05 | 1501.67 | 478.03 | 117.63 | 45.05 | 12.51 |
| Sample 1 ≤−60° C. | 24144.26 | 6836.83 | 1510.11 | 606.05 | 157.77 | 35.06 | 22.54 |
| Sample 2 −20° C. | 44356.72 | 16899.23 | 3591.21 | 748.80 | 175.30 | 42.57 | 12.52 |
| Sample 2 ≤−60° C. | 32438.61 | 9433.82 | 2036.02 | 688.69 | 152.76 | 40.07 | 22.54 |
| Sample 3 −20° C. | 51606.76 | 9498.93 | 3032.75 | 1570.22 | 250.43 | 75.13 | 55.10 |
| Sample 3 ≤−60° C. | 43041.95 | 9493.92 | 2874.97 | 1450.01 | 185.32 | 35.06 | 17.53 |
| Sample 4 ≤−60° C. | 31191.45 | 8807.73 | 1930.84 | 668.66 | 152.76 | 32.56 | 10.02 |

TABLE 23-continued

Particle concentration after 6 months at −20 ± 2° C. and ≤−60° C.

| Measurement | ≥1 μm | ≥2 μm | ≥5 μm | ≥10 μm | ≥25 μm | ≥50 μm | ≥70 μm |
|---|---|---|---|---|---|---|---|
| Sample 5 −20° C. | 82750.63 | 17525.31 | 7695.81 | 4299.94 | 558.47 | 50.09 | 25.04 |
| Sample 5 ≤−60° C. | 77216.06 | 19578.87 | 8812.74 | 4675.59 | 548.45 | 50.09 | 22.54 |

Results of osmolality measurements are shown in Table 24.

TABLE 24

Osmolality measurements

| Name and Formulation | mOsmol/kg |
|---|---|
| Buffer 1[7]: Chatham buffer + 0.005% PS80 | 990 |
| Buffer 2[7]: 20 mM His, 70 mM NaCl, 5% Sucrose, 0.005% PS80 | 309 |
| Buffer 3[7]: 20 mM His, 60 mM NaCl, 110 mM Mannit, 35 mM Trehalose Dihydrate, 0.005% PS80 | 296 |
| Buffer 4[7]: 10 mM His, 100 mM NaCl, 50 mM Glycine, 5% Trehalose Dihydrate, 0.005% PS80 | 386 |
| Buffer 5[7]: 15 mM Na3Cit buffer, 15 mM Glycine, 20 g Mannit, 10 g Trehalose Dihydrat, 0.005% PS80 | 212 |
| Buffer 6[7]: 80 mM TRIS, Dextran T10 and T40, 6.9% Sucrose. 0.005% PS80 | 417 |

In conclusion, there were no significant differences among the six formulations for AAV8 titration ELISA after 4 months at 5±3° C. and after 6 months at −20±2° C. and ≤−60° C. Appearance complies for Formulations 2-5, while a few particles formed for Formulation 1 and a slight yellow color was observed for Formulation 6. All formulations, except Formulation 6 and the control, showed stability during storage time for all temperatures as tested by SDS-PAGE (densiometric method). Based on appearance, subvisible particle assay (MFI) data, and osmolality values, Formulations 2, 3, and 4 were selected for further development.

Example 2

This example demonstrates the additional testing and further development of three formulations.

Formulations 2, 3, and 4 (Buffers 2, 3, and 4, Samples 2, 3, and 4) were manufactured as essentially described in Example 1. Briefly, a single lot was diluted with PBS/NaCl/Sorbitol buffer to general 90 ml. The solution was spiked with 0.005% Croda super refined PS80 and aliquoted into 3 parts. The buffer was changed to one of the three different buffers or control buffer via Slide-A-Lyzer dialysis cassettes and this step was repeated for a total of 3 times with 100 fold volume of the sample. The 3 different solutions were filled into 2 mL Schott Type I glass vials with a SiO₂ layer and stored at the temperatures described below.

In this example, "Buffer 1" refers to Formulation/Buffer/Sample 2 of Example 1, "Buffer 2" refers to Formulation/Buffer/Sample 4 of Example 1, "Buffer 3" refers to Formulation/Buffer/Sample 3 of Example 1, and "Buffer 4" refers to a PBS/NaCl/Sorbitol buffer control. For clarity, Tables 25-28 describe Buffers 1-3 and the PBS/NaCl/Sorbitol buffer control of this example.

TABLE 25

Buffer 1 (Formulation 2)

| Excipient | Concentration [mM] | Concentration g/kg buffer |
|---|---|---|
| L-histidine | 20 | 3.103 |
| NaCl | 70 | 4.09 |
| Sucrose | 5% | 50.00 |
| Croda super refined Tween 80 (PS80) | 0.005% | 0.05 |
| Purified water | | add to 1 kg |
| pH value | 7.5 | |

TABLE 26

Buffer 2 (Formulation 4)

| Excipient | Concentration [mM] | Concentration g/kg buffer |
|---|---|---|
| L-histidine | 10 | 1.552 |
| NaCl | 100 | 5.844 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | 7.0 ± 0.1 | |

TABLE 27

Buffer 3 (Formulation 3)

| Excipient | Concentration [mM] | Concentration g/kg buffer |
|---|---|---|
| L-histidine | 20 | 3.103 |
| NaCl | 60 | 3.506 |
| Mannitol | 110 | 20.039 |
| Trehalose Dihydrate | 35 | 13.24 |
| Croda super refined Tween 80 (PS80) | 0.005% | 0.05 |
| Purified water | | add to 1 kg |
| pH value | 7.0 ± 0.1 | |

TABLE 28

PBS/NaCl/Sorbitol Buffer Control

| Excipient | Concentration [mM] | Concentration g/kg buffer |
|---|---|---|
| Sodium chloride | 350 | 20.45 |
| Potassium chloride | 2.68 | 0.2 |
| Disodiumhydrogenphosphate-Dihydrate | 8.09 | 1.44 |
| Monopotassium phosphate | 1.47 | 0.2 |
| D-Sorbitol | 5% | 50.00 |
| Croda super refined Tween 80 (PS80) | 0.005% | 0.05 |
| 25% HCl | | pH adjustment |
| 1M NaOH | | |

TABLE 28-continued

PBS/NaCl/Sorbitol Buffer Control

| Excipient | Concentration [mM] | Concentration g/kg buffer |
|---|---|---|
| Purified water | | add to 1 kg |
| pH value | | 7.4 ± 0.3 |

Medium- to long-term stability studies at ° C. (set point: −80° C.) and at −20±2° C. for up to 5 months (0, 1, 2, 3, and 5 months) and at 5±3° C. for up to 4 months (0, 1, 2, and 4 months) were performed. The formulations were stored in 2 ml Schott Type I glass vials with a $SiO_2$ layer. Each vial was filled with 0.3 mL of a formulation. The analytical tests listed in Table 29 were performed and the test time points for each assay at the indicated storage temperatures are shown in Tables 30 and 31. A "-" in Table 30 or 31 means no samples were taken.

TABLE 29

Analytical assays

| Quality Attribute | Detection by analytical method/principle |
|---|---|
| General | Polysorbate 80 |
| | Appearance |
| | pH values |
| Activity | In vitro Biopotency |
| | In vivo Biopotency |
| | FIX-qPCR |
| Total particle titer (empty + full) | Total rAAV8 particle ELISA |
| AAV purity | SDS-PAGE (fluorescence staining, |

TABLE 29-continued

Analytical assays

| Quality Attribute | Detection by analytical method/principle |
|---|---|
| Chemical degradation | 4-12% BisTris gel with Flamingo Stain) |
| Physical degradation (damaged capsids or fragments) | WAX [Weak Anion Exchange HPLC] SEC [Size exclusion HPLC] |

TABLE 30

Study outline with storage at −20 ± 2° C. and ≤−60° C. (set point: −80° C.)

| Test | Sample Volume | Test Time Point [months] 0 | 1 | 2 | 3 | 5 | Total Number of Samples |
|---|---|---|---|---|---|---|---|
| SDS-PAGE (fluorescence staining, 4-12% BisTris gel with Flamingo Stain) | 0.3 ml | x | x | x | x | x | 36 |
| WAX [Weak Anion Exchange HPLC] | 0.3 ml | x | x | x | x | x | 36 |
| SEC [Size exclusion HPLC] | 0.3 ml | x | x | x | x | x | 36 |
| In vitro Biopotency | 0.3 ml | x | x | x | x | x | 36 |
| In vivo Biopotency | 0.3 ml | x | x | — | — | x | 20 |
| FIX-qPCR | 0.3 ml | x | x | x | x | x | 36 |
| Total rAAV8 particle ELISA | 2 × 0.3 ml | x | x | x | x | x | 72 |
| Appearance | 1 ml | x | x | — | — | — | 136 |
| pH value | | x | x | — | — | — | 12 |
| Polysorbate 80 | 0.3 ml | — | — | — | — | x | 3 |

TABLE 31

Study outline with storage at +5 ± 3° C.

| Test | Sample Volume | Test Time Point [months] 0 | 1 | 2 | 4 | Total Number of Samples |
|---|---|---|---|---|---|---|
| SDS-PAGE (fluorescence staining, 4-12% BisTris gel with Flamingo Stain) | 0.3 ml | x | x | x | x | 16 |
| WAX [Weak Anion Exchange HPLC] | 0.3 ml | x | x | x | x | 16 |
| SEC [Size exclusion HPLC] | 0.3 ml | x | x | x | x | 16 |
| In vitro Biopoteney | 0.3 ml | x | x | x | x | 16 |
| In vivo Biopotency | 0.3 ml | x | x | — | x | 12 |
| FIX-qPCR | 0.3 ml | x | x | x | x | 16 |
| Total rAAV8 particle ELISA | 2 × 0.3 ml | x | x | x | x | 32 |
| Appearance | 1 ml | x | x | x | x | 56 |
| pH value | | x | x | — | — | 8 |

Results of the ELISA are shown in Table 32. AAV8 titration ELISA showed a massive amount of material loss for Buffer 4 (control) during storage at 5±3° C. Compare $5.61 \times 10^{12}$ [cp/ml] at 0 months to $2.71 \times 10^{12}$ after 4 months. No additional losses were observed for the same material stored at −20±2° C. and ≤−60° C. Buffers and 1 and 2 did not exhibit any material loss. Buffer 3 showed a lower starting material amount that does not decrease during storage time.

TABLE 32

AAV8 titration ELISA

| AAV8 Titration ELISA [cp/ml] at +5 ± 3° C. | 0 months | 1 month at +5 ± 3° C. | 2 months at +5 ± 3° C. | 4 months at +5 ± 3° C. | |
|---|---|---|---|---|---|
| BUFFER 1 | 9.39E+12 | 7.46E+12 | 9.33E+12 | 8.56E+12 | |
| BUFFER 2 | 1.01E+13 | 7.46E+12 | 9.17E+12 | 9.90E+12 | |
| BUFFER 3 | 8.05E+12 | 6.69E+12 | 7.55E+12 | 8.03E+12 | |
| BUFFER 4 | 5.61E+12 | 4.80E+12 | 3.82E+12 | 2.71E+12 | |

| AAV8 Titration ELISA [cp/ml] at −20 ± 2° C. | 0 months | 1 month at −20 ± 2° C. | 2 months at −20 ± 2° C. | 3 months at −20 ± 2° C. | 5 months at −20 ± 2° C. |
|---|---|---|---|---|---|
| BUFFER 1 | 9.39E+12 | 7.59E+12 | 8.73E+12 | 8.67E+12 | 9.83E+12 |

| AAV8 Titration ELISA [cp/ml] at +5 ± 3° C. | 0 months | 1 month at +5 ± 3° C. | 2 months at +5 ± 3° C. | 3 months at +5 ± 3° C. | 4 months at +5 ± 3° C. |
|---|---|---|---|---|---|
| BUFFER 2 | 1.01E+13 | 7.81E+12 | 8.78E+12 | 9.17E+12 | 1.00E+13 |
| BUFFER 3 | 8.05E+12 | 6.60E+12 | 7.55E+12 | 7.52E+12 | 8.17E+12 |
| BUFFER 4 | 5.61E+12 | 5.35E+12 | 5.68E+12 | 5.17E+12 | 6.79E+12 |

| AAV8 Titration ELISA [cp/ml] at ≤−60° C. | 0 months | 1 month at ≤−60° C. | 2 months at ≤−60° C. | 3 months at ≤−60° C. | 5 months at ≤−60° C. |
|---|---|---|---|---|---|
| BUFFER 1 | 9.39E+12 | 7.35E+12 | 9.13E+12 | 8.58E+12 | 9.62E+12 |
| BUFFER 2 | 1.01E+13 | 7.35E+12 | 9.46E+12 | 8.82E+12 | 9.98E+12 |
| BUFFER 3 | 8.05E+12 | 6.14E+12 | 7.77E+12 | 7.22E+12 | 8.59E+12 |
| BUFFER 4 | 5.61E+12 | 4.91E+12 | 6.45E+12 | 5.26E+12 | 6.00E+12 |

The results of the qPCR are shown in Table 33. All data generated with this assay confirm the ELISA and in vitro biopotency assay. Buffer 4 shows a high amount of test variation.

TABLE 33

FIX-qPCR [vg/ml]

| FIX-qPCR [vg/ml] at +5 ± 3° C. | | | | |
|---|---|---|---|---|
| | 0 months | 1 month at +5 ± 3° C. | 2 months at +5 ± 3° C. | 4 months at +5 ± 3° C. |
| BUFFER 1 | 6.11E+12 | 4.34E+12 | 1.74E+12 | 4.65E+12 |
| BUFFER 2 | 4.34E+12 | 4.60E+12 | 5.16E+12 | 4.14E+12 |
| BUFFER 3 | 3.66E+12 | 3.53E+12 | 3.86E+12 | 3.49E+12 |
| BUFFER 4 | 1.62E+12 | 1.63E+12 | 1.92E+12 | 4.98E+12 |

| FIX-qPCR [vg/ml] at −20 ± 2° C. | | | | |
|---|---|---|---|---|
| | 0 months | 1 month at −20 ± 2° C. | 2 months at −20 ± 2° C. | 3 months at −20 ± 2° C. | 5 months at −20 ± 2° C. |
| BUFFER 1 | 6.11E+12 | 3.42E+12 | 4.42E+12 | 4.10E+12 | 4.07E+12 |
| BUFFER 2 | 4.34E+12 | 3.57E+12 | 4.12E+12 | 4.01E+12 | 4.20E+12 |
| BUFFER 3 | 3.66E+12 | 2.23E+12 | 3.44E+12 | 3.51E+12 | 3.79E+12 |
| BUFFER 4 | 1.62E+12 | 4.33E+12 | 2.70E+12 | 3.29E+12 | 2.06E+12 |

| FIX-qPCR [vg/ml] at ≤−60° C. | | | | |
|---|---|---|---|---|
| | 0 months | 1 month at ≤−60° C. | 2 months at ≤−60° C. | 3 months at ≤−60° C. | 5 months at ≤−60° C. |
| BUFFER 1 | 6.11E+12 | 4.59E+12 | 4.67E+12 | 4.06E+12 | 4.35E+12 |
| BUFFER 2 | 4.34E+12 | 3.78E+12 | 4.77E+12 | 2.78E+12 | 4.37E+12 |
| BUFFER 3 | 3.66E+12 | 2.57E+12 | 3.68E+12 | 3.48E+12 | 3.37E+12 |
| BUFFER 4 | 1.62E+12 | 1.47E+12 | 1.97E+12 | 1.60E+12 | 1.86E+12 |

The results of the % aggregate measurements are shown in Table 34. Decreasing aggregate values were seen after storage for 4 months at 5±3° C. Buffer 4 showed an increase from 1.55% to 3.39% after 3 months and no aggregates after 4 months. Buffer 3 reached a high of 6.64% after 2 months at −60° C. that dropped to 3.25% after 3 months and 3.94% after 5 months.

TABLE 34

| Aggregates [%] | | | | |
|---|---|---|---|---|
| Aggregates [%] at +5 ± 3° C. | | | | |
| | 0 months | 1 month at +5 ± 3° C. | 2 months at +5 ± 3° C. | 4 months at +5 ± 3° C. |
| BUFFER 1 | 2.39 | 2.34 | 2.26 | 1.40 |
| BUFFER 2 | 2.46 | 2.13 | 2.55 | 1.36 |
| BUFFER 3 | 2.65 | 2.49 | 2.79 | 1.39 |
| BUFFER 4 | 1.55 | 3.39 | 3.39 | 0.00 |
| Aggregates [%] at −20 ± 2° C. | | | | |
| | 0 months | 1 month at −20 ± 2° C. | 2 months at −20 ± 2° C. | 3 months at −20 ± 2° C. | 5 months at −20 ± 2° C. |
| BUFFER 1 | 2.39 | 2.35 | 2.49 | 2.46 | 2.81 |
| BUFFER 2 | 2.46 | 2.30 | 2.48 | 2.42 | 2.47 |
| BUFFER 3 | 2.65 | 2.62 | 2.91 | 2.79 | 2.85 |
| BUFFER 4 | 1.55 | 3.06 | 3.24 | 3.73 | 3.66 |
| Aggregates [%] at ≤−60° C. | | | | |
| | 0 months | 1 month at ≤−60° C. | 2 months at ≤−60° C. | 3 months at ≤−60° C. | 5 months at ≤−60° C. |
| BUFFER 1 | 2.39 | 2.24 | 2.26 | 2.12 | 2.56 |
| BUFFER 2 | 2.46 | 2.20 | 2.50 | 2.57 | 2.39 |
| BUFFER 3 | 2.65 | 3.39 | 6.64 | 3.25 | 3.94 |
| BUFFER 4 | 1.55 | 2.28 | 2.01 | | 2.90 |

The results of the weak anion exchange (WAX) assay which measures full capsids did not exhibit any meaningful differences for all testing time points and storage temperatures (Table 35).

TABLE 35

| Full Capsids [%] | | | | |
|---|---|---|---|---|
| Full Capsids [%] at +5 ± 3° C. | | | | |
| | 0 months | 1 month at +5 ± 3° C. | 2 months at +5 ± 3° C. | 4 months at +5 ± 3° C. |
| BUFFER 1 | 61 | 62 | 67 | 62 |
| BUFFER 2 | 62 | 64 | 65 | 61 |
| BUFFER 3 | 63 | 62 | 64 | 63 |
| BUFFER 4 | 62 | 62 | 66 | 58 |
| Full Capsids [%] at −20 ± 2° C. | | | | |
| | 0 months | 1 month at −20 ± 2° C. | 2 months at −20 ± 2° C. | 3 months at −20 ± 2° C. | 5 months at −20 ± 2° C. |
| BUFFER 1 | 61 | 64 | 68 | 63 | 62 |
| BUFFER 2 | 62 | 63 | 66 | 61 | 61 |
| BUFFER 3 | 63 | 62 | 66 | 63 | 61 |
| BUFFER 4 | 62 | 62 | 64 | 63 | 60 |
| Full Capsids [%] at ≤−60° C. | | | | |
| | 0 months | 1 month at ≤−60° C. | 2 months at ≤−60° C. | 3 months at ≤−60° C. | 5 months at ≤−60° C. |
| BUFFER 1 | 61 | 64 | 64 | 61 | 60 |
| BUFFER 2 | 62 | 62 | 65 | 63 | 63 |
| BUFFER 3 | 63 | 63 | 65 | 62 | 61 |
| BUFFER 4 | 62 | 63 | 66 | 62 | 61 |

The results of the in vitro biopotency assay are shown in Table 36. Similar fluctuating values are shown for Buffer 1, Buffer 2, and Buffer 3 in the range of test variation. Buffer 4 shows a high decrease after storage at 5±3° C. for 4 months. Comparable results were detected for all other buffers, testing time points and temperatures.

TABLE 36

In vitro Biopotency [BPU]

In vitro Biopotency [BPU] at +5 ± 3° C.

|  | 0 months | 1 month at +5 ± 3° C. | 2 months at +5 ± 3° C. | 4 months at +5 ± 3° C. |
| --- | --- | --- | --- | --- |
| BUFFER 1 | 1.05 | 0.87 | 1.05 | 1.22 |
| BUFFER 2 | 0.85 | 1.02 | 1.02 | 1.07 |
| BUFFER 3 | 0.78 | 0.90 | 1.14 | 1.20 |
| BUFFER 4 | 0.67 | 0.65 | 0.57 | 0.13 |

In vitro Biopotency [BPU] at −20 ± 2° C.

|  | 0 months | 1 month at −20 ± 2° C. | 2 months at −20 ± 2° C. | 3 months at −20 ± 2° C. | 5 months at −20 ± 2° C. |
| --- | --- | --- | --- | --- | --- |
| BUFFER 1 | 1.05 | 0.83 | 1.23 | 1.09 | 1.24 |
| BUFFER 2 | 0.85 | 0.84 | 1.11 | 0.97 | 1.35 |
| BUFFFR 3 | 0.78 | 0.68 | 0.94 | 1.13 | 1.25 |
| BUFFER 4 | 0.67 | 1.93 | 1.76 | 0.79 | 1.18 |

In vitro Biopotency [BPU] at ≤−60° C.

|  | 0 months | 1 month at ≤−60° C. | 2 months at ≤−60° C. | 3 months at ≤−60° C. | 5 months at ≤−60° C. |
| --- | --- | --- | --- | --- | --- |
| BUFFER 1 | 1.05 | 1.15 | 1.10 | 1.01 | 1.34 |
| BUFFER 2 | 0.85 | 1.09 | 0.80 | 0.96 | 1.21 |
| BUFFER 3 | 0.78 | 0.83 | 0.96 | 0.94 | 1.12 |
| BUFFER 4 | 0.67 | 0.80 | 0.98 | 0.68 | 1.08 |

The results of the in vivo biopotency assay are shown in Table 37. Results for Buffers 1-3 show fluctuating results in the range of test variation. Buffer 4 decreases from 3.70 [11.1/ml] at 0 months to 1.33 [11.1/ml] after 4 months at 5±3° C. and increases from 3.79 [11.1/ml] at 0 months to 6.73 [11.1/ml] after 4 months at ≤−60° C. Day 7 results were similar to Day 14 results. The results after 1 month storage at ≤−60° C. are taken as a reference value representing the 0 month for all storage temperatures.

TABLE 37

In vivo Biopotency [Iu/ml] day 14 results

| In vivo Biopotency [IU/ml] at +5 ± 3° C. | 0 months day 14 | 1 month at +5 ± 3° C., day 14 | 2 months at +5 ± 3° C., day 14 | 3 months at +5 ± 3° C., day 14 | 4 months at +5 ± 3° C., day 14 |
| --- | --- | --- | --- | --- | --- |
| BUFFER 1 | 3.48 ± 1.28 | 5.91 ± 1.33 | 4.82 ± 0.63 |  | 4.76 ± 0.55 |
| BUFFER 2 | 4.99 ± 0.74 | 5.49 ± 0.64 | 5.27 ± 0.84 |  | 5.36 ± 1.80 |
| BUFFER 3 | 4.43 ± 1.15 | 6.42 ± 0.89 | 4.64 ± 1.42 |  | 5.58 ± 0.68 |
| BUFFER 4 | 3.79 ± 0.70 | 3.43 ± 0.61 | 2.77 ± 0.44 |  | 1.33 ± 0.26 |

| In vivo Biopotency [IU/ml] at −20 ± 2° C. | 0 months day 14 | 1 month at −20 ± 2° C., day 14 | 2 months at −20 ± 2° C., day 14 | 3 months at −20 ± 2° C., day 14 | 4 months at −20 ± 2° C., day 14 | 5 months at −20 ± 2° C., day 14 |
| --- | --- | --- | --- | --- | --- | --- |
| BUFFER 1 | 3.48 ± 1.28 |  |  | 5.09 ± 2.25 | 4.97 ± 1.30 | 5.28 ± 0.55 |
| BUFFER 2 | 4.99 ± 0.74 |  |  | 5.85 ± 0.74 | 4.88 ± 1.44 | 5.04 ± 0.70 |
| BUFFER 3 | 4.43 ± 1.15 |  |  | 4.34 ± 1.62 | 5.16 ± 0.79 | 5.03 ± 1.00 |
| BUFFER 4 | 3.79 ± 0.70 |  |  | 3.42 ± 1.46 | 4.20 ± 1.74 | 4.39 ± 0.76 |

| In vivo Biopotency [IU/ml] at ≤−60° C. | 0 months day 14 | 1 month at ≤−60° C., day 14 | 2 months at ≤−60° C., day 14 | 3 months at ≤−60° C., day 14 | 4 months at ≤−60° C., day 14 | 5 months at ≤−60° C., day 14 |
| --- | --- | --- | --- | --- | --- | --- |
| BUFFER 1 | 3.48 ± 1.28 | 3.48 ± 1.28 |  |  |  | 5.99 ± 1.58 |
| BUFFER 2 | 4.99 ± 0.74 | 4.99 ± 0.74 |  |  |  | 5.68 ± 1.02 |

TABLE 37-continued

| | In vivo Biopotency [Iu/ml] day 14 results | | | |
|---|---|---|---|---|
| BUFFER 3 | 4.43 ± 1.15 | 4.43 ± 1.15 | | 4.63 ± 1.33 |
| BUFFER 4 | 3.79 ± 0.70 | 3.79 ± 0.70 | | 6.73 ± 0.90 |

TABLE 38

| In vivo Biopotency [IU/ml] day 7 results | | | | | |
|---|---|---|---|---|---|
| In vivo Biopotency [IU/ml] at ±5 ± 3° C. | 0 months day 7 | 1 month at ±5 ± 3° C., day 7 | 2 months at ±5 ± 3° C., day 7 | 3 months at ±5 ± 3° C., day 7 | 4 months at ±5 ± 3° C., day 7 |
| BUFFER 1 | 2.35 ± 0.79 | 3.86 ± 0.93 | 3.15 ± 0.29 | | 2.70 ± 0.32 |
| BUFFER 2 | 3.41 ± 0.55 | 3.31 ± 0.68 | 3.81 ± 0.74 | | 3.46 ± 0.23 |
| BUFFER 3 | 3.29 ± 0.25 | 3.58 ± 0.59 | 3.09 ± 0.76 | | 3.12 ± 0.36 |
| BUFFER 4 | 2.30 ± 0.48 | 2.00 ± 0.40 | 1.68 ± 0.30 | | 0.80 ± 0.04 |

| In vivo Biopotency [IU/ml] at −20 ± 2° C. | 0 months day 7 | 1 month at −20 ± 2° C., day 7 | 2 months at −20 ± 2° C., day 7 | 3 months at −20 ± 2° C., day 7 | 4 months at −20 ± 2° C., day 7 | 5 months at −20 ± 2° C., day 7 |
|---|---|---|---|---|---|---|
| BUFFER 1 | 2.35 ± 0.79 | | | 3.20 ± 1.40 | 2.91 ± 0.81 | 3.29 ± 0.56 |
| BUFFER 2 | 3.41 ± 0.55 | | | 3.60 ± 0.55 | 3.01 ± 0.80 | 3.01 ± 0.64 |
| BUFFER 3 | 3.29 ± 0.25 | | | 3.04 ± 1.11 | 3.12 ± 0.56 | 3.18 ± 0.69 |
| BUFFER 4 | 2.30 ± 0.48 | | | 1.84 ± 0.80 | 0.80 ± 0.04 | 2.46 ± 0.45 |

| In vivo Biopotency [IU/ml] at ≤−60° C. | 0 months day 7 | 1 month at ≤−60° C., day 7 | 2 months at ≤−60° C., day 7 | 3 months at ≤−60° C., day 7 | 4 months at ≤−60° C., day 7 | 5 months at ≤−60° C., day 7 |
|---|---|---|---|---|---|---|
| BUFFER 1 | 2.35 ± 0.79 | 2.35 ± 0.79 | | | | 4.02 ± 1.11 |
| BUFFER 2 | 3.41 ± 0.55 | 3.41 ± 0.55 | | | | 3.58 ± 1.07 |
| BUFFER 3 | 3.29 ± 0.25 | 3.29 ± 0.97 | | | | 2.67 ± 0.74 |
| BUFFER 4 | 2.30 ± 0.48 | 2.30 ± 0.48 | | | | 3.53 ± 0.46 |

The results of the SDS PAGE densiotometric assay are shown in Tables 39-44. No additional bands were observed during storage at 5±3° C. for up to 4 months and for storage at −20±2° C. and ≤−60° C. for up to 5 months.

TABLE 39

| | Purity and summary at 0 months storage | | | | |
|---|---|---|---|---|---|
| Vector protein | HT6AR00G (Ref) 10 μg/ml Lane 3 Band % | Sample 1 Mean Value L5-L7 Band % | Sample 2 Mean Value L9-L11 Band % | Sample 3 Mean Value L13-L15 Band % | Sample 4 Mean Value L17-L19 Band % |
| VP1 | 11.4 | 17.5 | 17.5 | 17.2 | 15.6 |
| VP2 | 10.9 | 19.9 | 20.9 | 20.4 | 18.8 |
| VP3 | 77.7 | 62.6 | 61.6 | 62.4 | 65.6 |
| SUM VP1 + VP2 + VP3 (Purity) | 100 | 100 | 100 | 100 | 100 |

TABLE 40

| | Purity and summary at 1 month storage | | | | | | |
|---|---|---|---|---|---|---|---|
| | Reference | +5 ± 3° C. 1 month | | | | −20 ± 2° C. 1 month | |
| Vector protein | HT6AR00G 10 μg/ml Lane 3 Band % | Buffer 1 Lane 5 Band % | Buffer 2 Lane 6 Band % | Buffer 3 Lane 7 Band % | Buffer 4 Lane 8 Band % | Buffer 1 Lane 10 Band % | Buffer 2 Lane 11 Band % |
| VP1 | 7.49 | 15.63 | 15.95 | 15.82 | 14.06 | 14.91 | 15.34 |
| VP2 | 10.96 | 18.16 | 18.18 | 18.56 | 16.12 | 17.05 | 18.33 |

TABLE 40-continued

| Purity and summary at 1 month storage | | | | | | | |
|---|---|---|---|---|---|---|---|
| VP3 | 81.54 | 66.21 | 65.88 | 65.62 | 69.82 | 68.04 | 66.32 |
| SUM VP1 + VP2 + VP3 (Purity) | 100 | 100 | 100 | 100 | 100 | 100 | 100 |

| | | −20 ± 2° C. 1 month | | −60 ± 2° C. 1 month | | | |
|---|---|---|---|---|---|---|---|
| Vector protein | | Buffer 3 Lane 12 Band % | Buffer 4 Lane 13 Band % | Buffer 1 Lane 15 Band % | Buffer 2 Lane 16 Band % | Buffer 3 Lane 17 Band % | Buffer 4 Lane 18 Band % |
| VP1 | | 15.72 | 14.22 | 15.31 | 15.27 | 14.99 | 14.35 |
| VP2 | | 18.14 | 17.65 | 19.18 | 19.48 | 18.33 | 17.36 |
| VP3 | | 66.14 | 68.13 | 65.51 | 65.25 | 66.69 | 68.29 |
| SUM VP1 + VP2 + VP3 (Purity) | | 100 | 100 | 100 | 100 | 100 | 100 |

TABLE 41

| Purity and summary at 2 months storage | | | | | | | | | | | | | |
|---|---|---|---|---|---|---|---|---|---|---|---|---|---|
| | Reference | +5 ± 3° C. 2 month | | | | −20 ± 2° C. 2 month | | | | −60 ± 2° C. 2 month | | | |
| Vector protein | HT6AR00G 10 μg/ml Lane 3 Band % | Buffer 1 Lane 5 Band % | Buffer 2 Lane 6 Band % | Buffer 3 Lane 7 Band % | Buffer 4 Lane 8 Band % | Buffer 1 Lane 10 Band % | Buffer 2 Lane 11 Band % | Buffer 3 Lane 12 Band % | Buffer 4 Lane 13 Band % | Buffer 1 Lane 15 Band % | Buffer 2 Lane 16 Band % | Buffer 3 Lane 17 Band % | Buffer 4 Lane 18 Band % |
| VP1 | 6.33 | 12.14 | 12.92 | 12.1 | 8.7 | 12.28 | 14.09 | 11.8 | 10.82 | 12.28 | 12.61 | 12.25 | 10.96 |
| VP2 | 7.46 | 19.79 | 19.24 | 17.78 | 14.62 | 18.84 | 18.26 | 16.97 | 15.28 | 18.77 | 19.45 | 17.87 | 16.08 |
| VP3 | 86.21 | 68.07 | 67.84 | 70.12 | 76.68 | 68.87 | 67.65 | 71.24 | 73.9 | 68.95 | 67.95 | 69.88 | 72.96 |
| SUM VP1 + VP2 + VP3 (Purity) | 100 | 100 | 100 | 100 | 100 | 100 | 100 | 100 | 100 | 100 | 100 | 100 | 100 |

TABLE 42

| Purity and summary at 3 months storage | | | | | | | | | |
|---|---|---|---|---|---|---|---|---|---|
| | Reference HT6AR00G | −20 ± 2° C. 3 month | | | | −60 ± 2° C. 3 month | | | |
| Vector protein | 10 μg/ml Lane 3 Band % | Buffer 1 Lane 5 Band % | Buffer 2 Lane 6 Band % | Buffer 3 Lane 7 Band % | Buffer 4 Lane 8 Band % | Buffer 1 Lane 10 Band % | Buffer 2 Lane 11 Band % | Buffer 3 Lane 12 Band % | Buffer 4 Lane 13 Band % |
| VP1 | 7.1 | 16.73 | 16.75 | 16.63 | 14.98 | 15.93 | 16 | 16.05 | 13.3 |
| VP2 | 6.56 | 20.94 | 21.9 | 21.02 | 17.77 | 21.07 | 21.89 | 19.95 | 16.14 |
| VP3 | 86.34 | 62.32 | 61.35 | 62.36 | 67.25 | 63 | 62.11 | 64.01 | 70.55 |
| SUM VP1 + VP2 + VP3 (Purity) | 100 | 100 | 100 | 100 | 100 | 100 | 100 | 100 | 100 |

TABLE 43

Purity and summary at 3 months storage

| Vector protein | Reference HT6AR00G 10 µg/ml Lane 3 Band % | +5 ± 3° C. 4 month | | | |
|---|---|---|---|---|---|
| | | Buffer 1 Lane 5 Band % | Buffer 2 Lane 6 Band % | Buffer 3 Lane 7 Band % | Buffer 4 Lane 8 Band % |
| VP1 | 12.13 | 16.16 | 17.45 | 16.44 | 11.35 |
| VP2 | 14.66 | 24.2 | 22.36 | 21.25 | 10.1 |
| VP3 | 73.2 | 59.65 | 60.19 | 62.3 | 78.55 |
| SUM VP1 + VP2 + VP3 (Purity) | 100 | 100 | 100 | 100 | 100 |

TABLE 44

Purity and summary at 5 months storage

| Vector protein | Reference HT6AR00G 10 µg/ml Lane 3 Band % | −20 ± 2° C. 5 month | | | | −60 ± 2° C. 5 month | | | |
|---|---|---|---|---|---|---|---|---|---|
| | | Buffer 1 Lane 5 Band % | Buffer 2 Lane 6 Band % | Buffer 3 Lane 7 Band % | Buffer 4 Lane 8 Band % | Buffer 1 Lane 10 Band % | Buffer 2 Lane 11 Band % | Buffer 3 Lane 12 Band % | Buffer 4 Lane 13 Band % |
| VP1 | 11.51 | 17.45 | 17.52 | 17.2 | 14.68 | 16.65 | 16.91 | 16.83 | 15.24 |
| VP2 | 16.44 | 22.43 | 23.27 | 22.5 | 19.7 | 22.46 | 22.69 | 22.38 | 20.38 |
| VP3 | 72.05 | 60.12 | 59.2 | 60.3 | 65.62 | 60.89 | 60.4 | 60.79 | 64.37 |
| SUM VP1 + VP2 + VP3 (Purity) | 100 | 100 | 100 | 100 | 100 | 100 | 100 | 100 | 100 |

Results of the appearance test are shown in Table 45-48, wherein the classification of particles inspection with an unaided eye were as follows: Level A=no particles visible; Level B=small single particles, barely visible; Level C=small single particles, easily visible; Level D many small particles, easily visible; and Level E=particles visible greater than or equal to 1 mm. The appearance of all samples after 1 month at 5±3° C., −20±2° C., and ≤−60° C. (set point: −80° C.) exhibited clear, colorless solutions without visible particles (denoted below and throughout the specification as "complies").

TABLE 45

Appearance during 48 hours at +25 ± 2° C.

| Appearance at +25 ± 2° C. | starting material | 1.5 hours | 3 hours | 4.5 hours | 6 hours | 24 hours | 48 hours |
|---|---|---|---|---|---|---|---|
| Concentration of AAV8 particles: 8.8E+12 [cp/ml] | | | | | | | |
| BUFFER 1 | A | A | A | A | A | A | A |
| BUFFER 2 | A | A | A | A | A | A | A |
| BUFFER 3 | A | A | A | A | A | A | A |
| BUFFER 4 | A | A | A | A-B | A-B | A | A-B |
| Concentration of AAV8 particles: 17.6E+12 [cp/ml] | | | | | | | |
| BUFFER 1 | A | A | A | A | A | A | A |
| BUFFER 2 | A | A | A | A | A | A | A |
| BUFFER 3 | A | A | A | A | A | A | A |
| BUFFER 4 | A | A | B | A-B | A-B | A-B | A-B |

TABLE 46

Appearance during 4 months at +5 ± 3° C.

| Appearance at +5 ± 3° C. | starting material short time after sterile filtration | starting material after 6 days at +5 ± 3° C. | 1 month | 2 months | 4 months | 4 months |
|---|---|---|---|---|---|---|
| Concentration of AAV8 particles: 8.8E+12 [cp/ml] | | | | | | |
| BUFFER 1 | A | complies to | A | A | A | complies |
| BUFFER 2 | A | criteria | A | A | A | complies |
| BUFFER 3 | A | | A | A | A | complies |

TABLE 46-continued

Appearance during 4 months at +5 ± 3° C.

| Appearance at +5 ± 3° C. | starting material short time after sterile filtration | starting material after 6 days at +5 ± 3° C. | 1 month | 2 months | 4 months | 4 months |
|---|---|---|---|---|---|---|
| BUFFER 4 | A | clear, colorless, with visible particles | A-B | A-B (2 fibers) | A-B (2 fibers) | complies |
| Concentration of AAV8 particles: 17.6E+12 [cp/ml] | | | | | | |
| BUFFER 1 | A | complies to criteria | A | A | A | complies |
| BUFFER 2 | A | | A | A | A | complies |
| BUFFER 3 | A | | A | A | A | complies |
| BUFFER 4 | A | clear, colorless, with visible particles | A-B | A-B (4 fibers) | A-B (4 fibers, >5 particles) | doesn't comply, white particles > 10 |

TABLE 47

Appearance during 6 months at −20 ± 2° C.

| Appearance at −20 ± 2° C. | starting material short time after sterile filtration | starting material after freezing at −20 ± 2° C. | starting material after freezing at −20 ± 2° C. | 1 month | 2 months | 3 months | 4 months | 6 months | 6 months |
|---|---|---|---|---|---|---|---|---|---|
| Concentration of AAV8 particles: 8.8E+12 [cp/ml] | | | | | | | | | |
| BUFFER 1 | A | A | complies | A | A | A | complies | A | complies |
| BUFFER 2 | A | A-B | complies | A | A | A | complies | A | complies |
| BUFFER 3 | A | A | complies | A | A | A-B | complies | A-B | complies |
| BUFFER 4 | A | B (1 particle) | clear, colorless, with visible particles | A-B | A-B (3 fibers) | B (>5 particles) | doesn't comply, white particles > 5 | C (>6 fibers) | clear, colorless solution with visible particles > 10 |
| Concentration of AAV8 particles: 17.6E+12 [cp/ml] | | | | | | | | | |
| BUFFER 1 | A | A-B | complies | A | A | A-B | complies | A-B | complies |
| BUFFER 2 | A | A-B | complies | A | A | A | complies | A | complies |
| BUFFER 3 | A | A-B | complies | A | A | A-B | complies | A-B | complies |
| BUFFER 4 | A | B | clear, colorless, with visible particles | A-B | A-B (2 fibers) | C (3 fibers, >5 particles) | doesn't comply, white particles > 5 | C (3 fibers, >10 particles) | clear, colorless solution with visible particles > 10 |

TABLE 48

Appearance during 6 months at 6° C.

| Appearance at ≤−60° C. | starting material short time after sterile filtration | starting material after freezing at − ≤ −60° C. | 1 month | 2 months | 3 months | 6 months | 6 months |
|---|---|---|---|---|---|---|---|
| Concentration of AAV8 particles: 8.8E+12 [cp/ml] | | | | | | | |
| BUFFER 1 | A | A | A | A | A | A | complies |
| BUFFER 2 | A | A | A | A | A | A | complies |

TABLE 48-continued

Appearance during 6 months at 6° C.

| Appearance at ≤−60° C. | starting material short time after sterile filtration | starting material after freezing at − ≤ −60° C. | 1 month | 2 months | 3 months | 6 months | 6 months |
|---|---|---|---|---|---|---|---|
| BUFFER 3 | A | A | A | A | A | A | complies |
| BUFFER 4 | A | A-B | A-B | A-B (3 fibers) | A-B (4 fibers) | A-B | complies |
| Concentration of AAV8 particles: 17.6E+12 [cp/ml] | | | | | | | |
| BUFFER 1 | A | A | A | A | A | A | complies |
| BUFFER 2 | A | A | A | A | A | A | complies |
| BUFFER 3 | A | A | A | A | A | A | complies |
| BUFFER 4 | A | A-B | A-B | A-B (3 fibers) | A-B (4 fibers) | B-C (>5 fibers) | clear, colorless solution with visible particles > 10 | pH values for the buffers/formulations at 0 months and after 1 month storage at the indicated temperatures are shown in Table 49.

TABLE 49 pH values at 1 month pH values at +5 ± 3° C.

| | target pH value | 0 months | 1 month at +5 ± 3° C. |
|---|---|---|---|
| BUFFER 1 | 7.5 | 7.45 | 7.46 |
| BUFFER 2 | 7.0 | 6.95 | 6.94 |
| BUFFER 3 | 7.0 | 7.00 | 6.98 |
| BUFFER 4 | 7.4 | 7.34 | 7.31 | pH values at −20 ± 2° C.

| | target pH value | 0 months | 1 month at −20 ± 2° C. |
|---|---|---|---|
| BUFFER 1 | 7.5 | 7.45 | 7.44 |
| BUFFER 2 | 7.0 | 6.95 | 6.96 |
| BUFFER 3 | 7.0 | 7.00 | 6.99 |
| BUFFER 4 | 7.4 | 7.34 | 7.33 | pH values at ≤−60° C.

| | target pH value | 0 months | 1 month at ≤−60° C. |
|---|---|---|---|
| BUFFER 1 | 7.5 | 7.45 | 7.43 |
| BUFFER 2 | 7.0 | 6.95 | 6.95 |
| BUFFER 3 | 7.0 | 7.00 | 6.98 |
| BUFFER 4 | 7.4 | 7.34 | 7.33 |

Polysorbate 80 (PS80) measurements were performed after storage for 5 months at ≤−60° C. The results (shown in Table 50) confirm the amount of PS80 was not reduced after storage for 5 months at ≤−60° C.

TABLE 50

Polysorbate 80 (HPLC method)

| Samples | µg/ml | recovery [%] |
|---|---|---|
| target concentration | 50 | 100% |
| sample 1 (Buffer 1 - Formulation 2) | 62.6 | 125% |
| sample 2 (Buffer 2 - Formulation 4) | 65.7 | 131% |
| sample 3 (Buffer 3 - Formulation 3) | 47.8 | 96% |

Based on the data in this study, no significant different was seen in the stability profile of AAV8 when formulated in any one of the three buffers/formulations tested. Therefore, all three may be considered suitable for the storage of AAV8 gene therapy products.

Example 3

This example demonstrates an additional investigation of two formulations for their adsorption to the inner surfaces of different vials and tubes.

Buffers 1 (Formulation 2) and 2 (Formulation 4) described in Example 2 were tested for adsorption to the inner surfaces of different vials and tubes. Buffer 1 ($1717.37 \times 10^{11}$ cp/ml) and Buffer 2 ($1431.94 \times 10^{11}$ cp/ml) were diluted to a target concentration of $1.1 \times 10^{13}$ cp/ml and sterile filtered with a PALL EKV filter. The samples were loaded into 2 ml glass vials and frozen, for future reference. The materials were then filled into vials and tubes as described in Table 51.

TABLE 51

| Sample container | Filing volume |
|---|---|
| 2 ml SiO$_2$ glass vial item number 3000375 | 0.3 ml |
| 10 ml SiO$_2$ glass vial item number 3000727 | 5.6 ml |
| 1.8 ml Nunc ® Cryo Tubes (PP) | 0.5 ml |
| 0.5 ml Eppendorf safe lock tubes ® (PP) | 0.2 ml |
| 1.5 ml Eppendorf safe lock tubes ® (PP) | 0.5 ml |
| 0.5 ml Eppendorf Protein LoBind tubes ® (PP) | 0.2 ml |
| 1.5 ml Eppendorf Protein LoBind tubes ® (PP) | 0.5 ml |

The samples were stored at 25±2° C. for 8 hours and then tested via PDTS/AAV8 titration ELISA. The results of the assay are shown in Table 52.

TABLE 52

| storage container | Buffer 1 [cp/ml] | Recovery [%] | Buffer2 [cp/ml] | Recovery [%] |
|---|---|---|---|---|
| 2 ml SiO$_2$ vial, starting mateial | 1.61E+13 | 100 | 1.04E+13 | 100 |
| after 8 hours at +25 ± 2° C. | | | | |
| 2 ml SiO$_2$ vial | 1.53E+13 | 95 | 1.05E+13 | 101 |
| 10 ml SiO$_2$ vial | 1.61E+13 | 100 | 1.03E+13 | 99 |
| 1.8 ml Nunc | 1.56E+13 | 97 | 1.03E+13 | 99 |
| 0.5 ml safe lock tube | 1.60E+13 | 99 | 1.01E+13 | 97 |
| 1.5 ml safe lock tube | 1.69E+13 | 105 | 1.06E+13 | 102 |
| 0.5 ml LowBind tube | 1.57E+13 | 97 | 9.85E+12 | 95 |
| 1.5 ml LowBind tube | 1.62E+13 | 100 | 1.05E+13 | 101 |

These results demonstrate that greater than 90% of the starting gene therapy material is recoverable from the 2 ml SiO$_2$ vials. No adsorption was seen, and no significant difference was seen among the two test buffers.

Example 4

This example demonstrates the stability of various AAV subtypes in Formulation 4.

AAV subtypes AAV 2, AAV 5, AAV 8, and AAV 9 were produced (University of Massachusetts at Worcester Medical School Vector Core Facility) and stored in Formulation 4 (as described in Examples 1-3), then tested for appearance to confirm no visible particles are generated and by ITR-qPCR to quantify vector genome for dosing in in vitro biopotency assay. These AAV subtypes each comprised an eGFP package insert that encoded Green Fluorescence Protein (CB6-Pl-eGFP). Testing was conducted at time point 0 and again at 6 weeks after storage at +5±3° C.

Two milliliter samples provided in a PBS based buffer (1×PBS+0.001% Pluronic F+68) with concentration of >5E+12 vg/ml AAV particles were thawed at ambient temperature and diluted to 4 ml (approximately >2.5 E+12 vg/ml) with Formulation 4. The approximately 0.0025% Polysorbate 80 from Formulation 4 prevented excessive material loss via adsorption (e.g., on the inner surfaces of the equipment). Total buffer of each of the samples were changed to Formulation 4 using Slide-A-Lyzer® 10K dialysis cassettes, and this step was performed three times with 100-fold volume, with dialysis taking place for a minimum of 4 hours for each step. After the buffer was changed to Formulation 4, the samples were taken for the initial 0 weeks testing time point and then storage at +5±3° C. for 6 weeks.

There were no visible particles observed for the different AAV subtypes stored in Formulation 4, even after storage for 6 weeks (Table 53). Thus, it is possible that the excipients observed at time 0 were resolved by 6 weeks.

TABLE 53

Appearance during storage in Formulation 4 at +5 ± 3° C.

| | Testing Time Points | |
|---|---|---|
| Subtype | 0 weeks | 6 weeks |
| AAV2 | Colorless solution without particles, cloudy | |
| AAV5 | Colorless solution without particles, very slightly cloudy | Clear colorless solution without particles |
| AAV8 | Colorless solution without particles, slightly cloudy | Clear colorless solution without particles |
| AAV9 | Clear colorless solution without particles | Clear colorless solution without particles |

While the recovery of AAV2 was low, which could be due to the variability of the ITR-qPCR assay (ITR-qPCR assay has test variations of ±0.5 log), the other AAV subtypes are stable for the 6 weeks tested. Use of Formulation 4 resulted in surprising stability of the AAV8 subtype.

TABLE 54

ITR-qPCR [vg/ml] during storage in Formulation 4 at +5 ± 3° C.

| Subtype | ITR-qPCR [vg/ml], 0 weeks | ITR-qPCR [vg/ml], 6 weeks | Recovery [%] After 6 weeks |
|---|---|---|---|
| AAV2 | 6.45E+10 | 2.65E+10 | 41 |
| AAV5 | 1.64E+12 | 1.44E+12 | 88 |
| AAV8 | 1.85E+10 | 2.11E+10 | 114 |
| AAV9 | 6.38E+11 | 5.24E+11 | 82 |

Example 5

This example demonstrates the feasibility of lyophilizing AAV formulations, in particular lyophilization of AAV in Formulation 4.

The AAV Formulation 4 was lyophilized and stored for up to 10 months at +5±3° C. Briefly, AAV8 containing gene therapy material was produced and lyophilized before storing vials containing the lyophilized material at +5±3° C. (controlled with the Eurotherm System linked to the SIZ). At each testing time point (1, 2, 3, 6 and 10) one vial was reconstituted with 5.5 ml purified water and the liquid was aliquoted according to Table 55. Lyophilization was performed two times with the buffer "Formulation 4" only and after those experiments the lyophilization was performed with active gene therapy material in Formulation 4. The vials with active gene therapy material were placed in front, middle or rear on the shelf. The gaps were closed with the same SiO$_2$ glass vials filled with Formulation 4 without the AAV.

TABLE 55

Study outline with storage at +5 ± 3° C.

| Test | Sample volume | Test time point [months] | | | | | Total number of samples | Acceptance criteria |
|---|---|---|---|---|---|---|---|---|
| | | 1 | 2 | 3 | 6 | 10 | | |
| SDS-PAGE (flourescence staining, 4-12% BisTris gel with Flamingo Stain) | 0.2 ml | x | x | x | x | x | 5 | report result |

TABLE 55-continued

Study outline with storage at +5 ± 3° C.

| Test | Sample volume | Test time point [months] | | | | | Total number of samples | Acceptance criteria |
| --- | --- | --- | --- | --- | --- | --- | --- | --- |
| | | 1 | 2 | 3 | 6 | 10 | | |
| WAX [Weak Anion Exchange HPLC] | 0.2 ml | x | x | x | x | x | 5 | |
| SEC [Size exclusion HPLC] | 0.2 ml | x | x | x | x | x | 5 | |
| In vitro Biopotency | 0.5 ml | x | x | x | x | x | 5 | |
| Appearance | 2 ml | x | x | x | x | x | 5 | |
| pH value | | x | x | x | x | x | | |
| In vivo Biopotency | 0.5 ml | x | x | x | x | x | 5 | |
| FIX-qPCR | 0.2 ml | x | x | x | x | x | 5 | |
| Total rAAV8 particle ELISA | 2 × 0.2 ml | x | x | x | x | x | 10 | |

Measurements were taken of different parameters before and after lyophilization. For each measurement, an average of three measurements (front, middle, and rear sample) was reported in Table 56. No significant differences were found for the parameters tested, except for the residual moisture. The residual moisture was 0.7% for the sample in the front, where drying occurs faster than rear where 3.6% was detected. The vial in the middle had 3.7% residual moisture.

TABLE 56A

Different parameters for gene therapy material after lyophilization

| Stability of Lyophilized Gene Therapy Product | AAV8 Titration ELISA [cp/ml] | FIX-qPCR [vg/ml] | In vitro Biopotency [BPU] | In vivo Biopotency, 14 days [IU/ml] | Appearance | pH | residual moisture | Aggregates [%] | WAX, full capsids [%] |
| --- | --- | --- | --- | --- | --- | --- | --- | --- | --- |
| Starting Material Before Lyo | 1.30E+13 | 4.99E+12 | 1.27 | 2.64 | Clear colorless solution without particles | | | 3.1 | 5.5 |
| FRONT | 1.21E+13 | 2.73E+12 | 1.24 | 2.91 | Clear colorless solution without particles | 7.02 | 0.7 | 4.2 | 50 |
| MIDDLE | 1.29E+13 | 4.02E+12 | 1.31 | 2.24 | clear colorless solution with 1 visible particle (fiber with 2-3 mm) | 7.02 | 3.7 | 3.8 | 57 |
| REAR | 1.16E+13 | 3.99E+12 | 1.45 | 2.34 | Clear colorless solution without particles | 7.02 | 3.6 | 4.2 | 56 |

TABLE 56B

Different parameters for gene therapy material after lyophilization, recovery [%]

| Recovery [%] | AAV8 Titration ELISA | FIX-qPCR | In vitro Biopotency | In vivo Biopotency, 14 days |
| --- | --- | --- | --- | --- |
| Starting Material Before Lyo | 100 | 100 | 100 | 100 |
| FRONT | 93 | 55 | 98 | 110 |
| MIDDLE | 99 | 81 | 103 | 85 |
| REAR | 89 | 80 | 114 | 89 |

TABLE 57

Different parameters for gene therapy material after storage as lyocakes for up to 10 months at +5 ± 3° C.

| Formulation 4 | | Appearance | pH value | AAV8 Titration ELISA [cp/ml] | recovery [%] | FIX-qPCR [vg/ml] | recovery [%] |
|---|---|---|---|---|---|---|---|
| Place on the shelf during lyophilisation | Starting Material Before Lyo. | Complies | | 1.30E+13 | 100 | 4.99E+12 | 100 |
| | After Lyo. | Front: Clear colorless, solution without particles, Middle: clear colorless solution with 1 visible particle (fiber with 2-3 mm), Rear: Clear colorless solution without particles | 7.02 | 1.22E+13 | 94 | 3.58E+12 | 72 |
| front left | 1 month | Clear colorless solution without particles | 7.03 | 1.16E+13 | 89 | 1.64E+12 | 33 |
| front right | 2 months | Clear colorless solution with many visible particles | 7.05 | 1.14E+13 | 88 | 3.71E+12 | 74 |
| middle | 3 months | Clear colorless solution without particles | 7.03 | 1.15E+13 | 89 | 3.07E+12 | 62 |
| front right | 6 months | Clear colorless solution without particles | 7.09 | 1.20E+13 | 92 | 3.97E+12 | 80 |
| Rear right | 10 months | Clear colorless solution without particles | 7.07 | 1.07E+13 | 83 | 4.22E+12 | 85 |

| Formulation 4 | | In vitro Biopotency [BPU] | recovery [%] | Aggregate [%] | WAX, full capsids [%] | In vivo BP, 14 days | In vivo BP, 14 days, recovery [%] |
|---|---|---|---|---|---|---|---|
| Place on the shelf during lyophilisation | Starting Material Before Lyo. | 1.27 | 100 | 3.1 | 55 | 2.64 | 100 |
| | After Lyo. | 1.33 | 105 | 4.1 | 54 | 2.50 | 95 |
| front left | 1 month | 0.89 | 70 | 3.9 | 55 | 1.76 | 67 |
| front right | 2 months | 0.95 | 75 | 4.1 | 50 | 2.14 | 81 |
| middle | 3 months | 0.89 | 70 | 4.0 | 59 | 2.02 | 77 |
| front right | 6 months | 0.81 | 64 | 4.6 | 55 | 1.72 | 65 |
| Rear right | 10 months | 0.89 | 70 | 3.9 | 52 | — | |

In conclusion, a recovery of 85% was obtained at the 10 month time point. The in vitro biopotency (recovery of 70% after 10 months) as well as the in vivo biopotency (recovery of 65% after 6 months) did not show losses directly after lyophilization, but after 1 month of storage there was a slight decrease. However, no further decrease in activity was seen by the 10 month time point. The percentages of full capsids as well as the results for the aggregates were stable.

Example 6

This example demonstrates additional testing and further development of the lyophilized formulations.

Four different formulations with different NaCl concentrations were examined with two different speeds of lyophilization (Tables 58-61). Briefly, the lyophilization programs differed in their temperature ramp for −55° C. to +2° C. during primary drying. In one cycle, the temperature increased over a period of 1.5 hours (Program 1), while in the other cycle the temperature increased over 12 hours (Program 2).

TABLE 58

| Formulation 4 | | |
|---|---|---|
| Excipient | Concentration [mM] | Concentration g/kg buffer |
| L-histidine | 10 | 1.552 |
| NaCl | 100 | 5.844 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | 7.0 ± 0.1 | |

TABLE 59

| Formulation 7 | | |
|---|---|---|
| Excipient | Concentration [mM] | Concentration/kg buffer |
| L-histidine | 10 | 1.552 |
| NaCl | 80 | 4.675 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | 7.0 ± 0.1 | |

TABLE 60

Formulation 8

| Excipient | Concentration [mM] | Concentration g/kg buffer |
|---|---|---|
| L-histidine | 10 | 1.552 |
| NaCl | 70 | 4.091 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | | 7.0 ± 0.1 |

TABLE 61

Formulation 9

| Excipient | Concentration [mM] | Concentration g/kg buffer |
|---|---|---|
| L-histidine | 10 | 1.552 |
| NaCl | 60 | 3.506 |
| Glycine | 50 | 3.754 |

TABLE 61-continued

Formulation 9

| Excipient | Concentration [mM] | Concentration g/kg buffer |
|---|---|---|
| Trehalose Dihydrate | 5% | 50 |
| Croda super refined Tween 80 | 0.005% | 0.05 |
| Purified water | | add to 1 kg |
| pH value | | 7.0 ± 0.1 |

The gene therapy material was thawed and pooled, and 29.2 ml of the pooled material was filled into Slide-A-Lyzer® 10K dialysis cassettes. The buffer was changed to either Formulation 4, 7, 8, or 9 as disclosed above. All samples were dialyzed three times in a 100-fold volume for a minimum of three hours. After dialysis, 5.5 ml of each of the material were filed into 10 ml $SiO_2$ vials. Before lyophilization, lyophilization stoppers were set on the glass vials without closing them. The lyophilized products were stored at +5±3° C. for up to 12 months.

The lower the NaCl concentrations, the lower the residual moisture was (Table 62).

TABLE 62

Comparison of residual moisture [%] directly after lyophilization

| Residual Moisture NaCl concentration/ program | Front 30/2 buffer | Front 30/2 active material | Middle 30/2 buffer | Middle 30/2 active material | Middle 30/2a buffer | Rear 30/2 buffer | Rear 30/2 active material |
|---|---|---|---|---|---|---|---|
| 100 mM | 2.4 | 3.2 | 2.1 | 2.8 | 3.7 | 2.7 | 2.5 |
| 80 mM | 2.1 | 1.7 | 1.6 | 1.7 | 2.7 | 1.8 | 2.1 |
| 70 mM | 1.6 | 1.8 | 1.5 | 1.8 | 2.2 | 1.8 | 1.9 |
| 60 mM | 1.2 | 1.2 | 1.3 | 0.9 | 1.4 | 1.2 | 1.3 |

The lyophilized products were stored at +5±3° C. for up to twelve months and tested for activity, total particle titer (empty+full), purity, degradation, and pH (Tables 63 and 64). At each testing time point (0, 1, 3, 6, and 12 months) one vial was reconstituted with 5.5 purified water and the liquid was aliquoted according to Table 63. Samples were frozen at −60° C. (set point: −80° C.) were tested. After lyophilization, no meaningful difference of values was detected and all data were found to be within the assay variation.

TABLE 63

Study outline for samples stored at +5 ± 3° C.

| Test | Sample volume | Test time point [months] 0 | 1 | 3 | 6 | 12 | Total number of samples | Acceptance criteria |
|---|---|---|---|---|---|---|---|---|
| SDS-PAGE (fluorescence staining, 4-12% BisTris gel with Flamingo Stain) | 0.2 ml | x | x | x | x | x | 40 | report result |
| WAX [Weak Anion Exchange HPLC] | 0.2 ml | x | x | x | x | x | 40 | |
| SEC [Size exclusion HPLC] | 0.2 ml | x | x | x | x | x | 40 | |
| Appearance | 2 ml | x | x | x | x | x | 40 | |
| pH value | | x | x | x | x | x | | |
| In vitro Biopotency | 0.5 ml | x | x | x | x | x | 40 | |
| In vivo Biopotency | 0.5 ml | x | x | — | x | x | minimum of 8 (36) | |

TABLE 63-continued

Study outline for samples stored at +5 ± 3° C.

| Test | Sample volume | Test time point [months] 0 | 1 | 3 | 6 | 12 | Total number of samples | Acceptance criteria |
|---|---|---|---|---|---|---|---|---|
| FIX-qPCR | 0.2 ml | x | x | x | x | x | 40 | |
| Total rAAV8 particle ELISA | 2 × 0.2 ml | x | x | x | x | x | 80 | |
| Residual moisture | 1 vial | x | x | x | x | x | 12 | |
| Reconstitution time | 1 vial | x | x | x | x | x | 40 | |

TABLE 64

Program 1 Results

| NaCl concentration/ parameter | AAV8 particle ELISA [vp/ml] | FIX-qPCR [vg/ml] | In vitro Biopot., dosage FIX-qPCR [BPU] | In vitro Biopot., dosage AAV8-ELISA Titer [BPU] | % of full capsids [%] | Aggreg. [%] | pH | Appearance |
|---|---|---|---|---|---|---|---|---|
| Starting Material (100 mM) | 1.39E+13 | | | | 61 | 2.3 | 7.00 | Clear colorless solution without particles |
| 100 mM | 1.17E+13 | 4.80E+12 | 0.75 | 0.68 | 63 | 3.5 | 7.00 | Clear colorless solution without particles |
| 80 mM | 1.08E+13 | 5.06E+12 | 0.70 | 0.75 | 57 | 4.1 | 7.02 | Clear colorless solution without particles |
| 70 mM | 1.20E+13 | 4.17E+12 | 0.77 | 0.74 | 54 | 4.1 | 7.00 | Clear colorless solution without particles |
| 60 mM | 1.32E+13 | 4.73E+12 | 0.67 | 0.68 | 55 | 3.9 | 7.04 | Clear colorless solution without particles |

In summary, Program 1 was the more aggressive program, but it gave the more compact and homogenous lyocakes. The lower the NaCl concentration was the lower the values for the residual moisture. The appearance complied with "clear, colorless solution without visible particles" for the starting material as well as for each NaCl concentration after dialysis, lyophilization and reconstitution. pH measurements, AAV8 particle ELISA, FIX-qPCR and the in vitro biopotency assay results showed similar values for each NaCl concentration. The WAX assay (percentage of full capsids) showed test variations within 54% to 63% (Table 69). Aggregates showed an increase from 2.3% for the untreated starting material to 3.5% and 4.1% for the dialyzed and lyophilized gene therapy material. Lyocakes for each NaCl concentration are white, compact and homogenous.

Example 7

This example demonstrates additional formulations.
Formulations 10 and 11 were manufactured as essentially described in Example 1.

TABLE 65

Formulation 10

| Excipient | Concentration [mM] | Concentration g/kg buffer |
|---|---|---|
| L-histidine | 10 | 1.552 |
| NaCl | 30 | 1.753 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | 7.0 ± 0.1 | |

TABLE 66

Formulation 11

| Excipient | Concentration [mM] | Concentration/kg buffer |
| --- | --- | --- |
| L-histidine | 10 | 1.552 |
| NaCl | 0 | 0 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | 7.0 ± 0.1 | |

Example 8

This example demonstrates additional formulations.

Formulations 12-15 are manufactured as essentially described in Example 1.

TABLE 67

Formulation 12

| Excipient | Concentration [mM] | Concentration g/kg buffer |
| --- | --- | --- |
| L-histidine | 10 | 1.552 |
| NaCl | 50 | 2.922 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | 7.0 ± 0.1 | |

TABLE 68

Formulation 13

| Excipient | Concentration [mM] | Concentration g/kg buffer |
| --- | --- | --- |
| L-histidine | 10 | 1.552 |
| NaCl | 40 | 2.338 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | 7.0 ± 0.1 | |

TABLE 69

Formulation 14

| Excipient | Concentration [mM] | Concentration g/kg buffer |
| --- | --- | --- |
| L-histidine | 10 | 1.552 |
| NaCl | 20 | 1.169 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | 7.0 ± 0.1 | |

TABLE 70

Formulation 15

| Excipient | Concentration [mM] | Concentration/kg buffer |
| --- | --- | --- |
| L-histidine | 10 | 1.552 |
| NaCl | 10 | 0.584 |
| Glycine | 50 | 3.754 |
| Trehalose Dihydrate | 5% | 50 |
| Croda super refined Tween 80 | 0.005% | 0.05 |
| Purified water | | add to 1 kg |
| pH value | 7.0 ± 0.1 | |

All references, including publications, patent applications, and patents, cited herein are hereby incorporated by reference to the same extent as if each reference were individually and specifically indicated to be incorporated by reference and were set forth in its entirety herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed:

1. A pharmaceutical composition comprising adeno-associated virus (AAV) and a buffering composition consisting of:
   i) about 5 mM to about 25 mM of a buffering agent selected from the group consisting of histidine, arginine, lysine, and a combination thereof;
   ii) about 50 mM to about 150 mM of a pharmaceutically acceptable salt selected from the group consisting of a sodium salt, an ammonium salt, a potassium salt, a cesium salt, an amine salt, and a combination thereof;
   iii) about 0.001% (w/v) to about 0.01% (w/v) of a non-ionic surfactant;
   iv) about 1% (w/v) to about 10% (w/v) of a sugar, a sugar alcohol, or a combination thereof; and
   v) about 30 mM to about 70 mM of glycine.

2. A pharmaceutical composition for lyophilization comprising adeno-associated virus (AAV) and a buffering composition consisting of:
   i) about 5 mM to about 25 mM of a buffering agent selected from the group consisting of histidine, arginine, lysine, and a combination thereof;
   ii) about 30 mM to about 100 mM of a pharmaceutically acceptable salt selected from the group consisting of a sodium salt, an ammonium salt, a potassium salt, a cesium salt, an amine salt, and a combination thereof;

iii) about 0.001% (w/v) to about 0.01% (w/v) of a non-ionic surfactant;

iv) about 1% (w/v) to about 10% (w/v) of a sugar, sugar alcohol, or combination thereof; and v) about 30 mM to about 70 mM of glycine.

3. The pharmaceutical composition of claim 1, wherein the pharmaceutically acceptable salt is a sodium salt, ammonium salt or potassium salt.

4. The pharmaceutical composition of claim 1, wherein the buffering composition has a pH of about 6.5 to about 9.0.

5. The pharmaceutical composition of claim 4, wherein the buffering composition has a pH of about 7.0 or about 7.5.

6. The pharmaceutical composition of claim 1, wherein the buffering agent is at a concentration of about 5 mM to about 15 mM, about 10 mM to about 20 mM, or about 15 mM to about 25 mM.

7. The pharmaceutical composition of claim 6, wherein the buffering agent is at a concentration of about 10 mM to about 20 mM.

8. The pharmaceutical composition of claim 1, wherein the pharmaceutically acceptable salt is at a concentration of about 50 mM to about 120 mM.

9. The pharmaceutical composition of claim 1, wherein the pharmaceutically acceptable salt is at a concentration of about 100 mM, about 80 mM, about 70 mM, about 60 mM, or about 50 mM.

10. The pharmaceutical composition of claim 1, wherein the non-ionic surfactant is in an amount from about 0.0025% (w/v) to about 0.0075% (w/v).

11. The pharmaceutical composition of claim 10, wherein the non-ionic surfactant is in an amount of about 0.005% (w/v).

12. The pharmaceutical composition of claim 1, wherein the sugar is in an amount of about 2.5% (w/v) to about 7.5% (w/v) or about 1% (w/v) to about 5% (w/v).

13. The pharmaceutical composition of claim 12, wherein the sugar is in an amount of about 5% (w/v).

14. The pharmaceutical composition of claim 1, wherein the glycine is in an amount of about 35 mM to about 65 mM.

15. The pharmaceutical composition of claim 14, wherein the glycine is in an amount of about 45 mM to about 55 mM.

16. The pharmaceutical composition of claim 15, wherein the glycine is in an amount of about 50 mM.

17. The pharmaceutical composition of claim 1, wherein the sugar alcohol is mannitol.

18. The pharmaceutical composition of claim 1, wherein the buffering composition does not comprise dextran.

19. The pharmaceutical composition of claim 1, wherein the buffering composition consisting of:

i) about 10 mM of a buffering agent that is histidine, arginine, lysine, or a combination thereof;

ii) about 100 mM of a pharmaceutically acceptable salt that is a sodium salt, an ammonium salt, a potassium salt, or a combination thereof;

iii) about 0.005% (w/v) of a non-ionic surfactant;

iv) about 5% (w/v) of a sugar, a sugar alcohol, or a combination thereof; and v) about 50 mM glycine.

20. The pharmaceutical composition of claim 1, wherein the buffering composition consisting of:

i) about 10 mM histidine;

ii) about 100 mM of a pharmaceutically acceptable salt that is a sodium salt, an ammonium salt, a potassium salt, or a combination thereof;

iii) about 0.005% (w/v) of a non-ionic surfactant;

iv) about 5% (w/v) of a sugar, a sugar alcohol, or a combination thereof; and v) about 50 mM glycine.

21. The pharmaceutical composition of claim 1, wherein the buffering agent is L-histidine.

22. The pharmaceutical composition of claim 1, wherein the pharmaceutically acceptable salt is sodium chloride.

23. The pharmaceutical composition of claim 1, wherein the non-ionic surfactant is Polysorbate 80 (PS80).

24. The pharmaceutical composition of claim 1, wherein the sugar is sucrose, trehalose, or both sucrose and trehalose.

25. The pharmaceutical composition of claim 1, wherein the AAV is at least one of AAV1, AAV2, AAV3, AAV4, AAV5, AAV6, AAV7, AAV8, AAV9, or AAV10.

26. The pharmaceutical composition of claim 1, wherein the composition is liquid or lyophilized.

27. A method of treating a bleeding disorder or disease in a subject, comprising administering to the subject a pharmaceutical composition of claim 1 in an amount effective to treat the bleeding disorder or disease.

* * * * *